United States Patent [19]
Chapman et al.

[11] Patent Number: 6,081,766
[45] Date of Patent: *Jun. 27, 2000

[54] MACHINE-LEARNING APPROACH TO MODELING BIOLOGICAL ACTIVITY FOR MOLECULAR DESIGN AND TO MODELING OTHER CHARACTERISTICS

[75] Inventors: David Chapman; Roger Critchlow, both of San Francisco, Calif.; Thomas Glen Dietterich, Corvalis, Oreg.; Ajay N. Jain, San Mateo; Richard H. Lathrop, Irvine, both of Calif.; Tomas Lozano-Perez, West Newton, Mass.

[73] Assignee: Axys Pharmaceuticals, Inc., South San Francisco, Calif.

[*] Notice: This patent is subject to a terminal disclaimer.

[21] Appl. No.: 08/583,000

[22] PCT Filed: May 20, 1994

[86] PCT No.: PCT/US94/05877

§ 371 Date: Apr. 11, 1996

§ 102(e) Date: Apr. 11, 1996

[87] PCT Pub. No.: WO94/28504

PCT Pub. Date: Dec. 8, 1994

Related U.S. Application Data

[63] Continuation-in-part of application No. 08/066,389, May 21, 1993, abandoned.

[51] Int. Cl.$^7$ ..................................................... G06F 17/00
[52] U.S. Cl. ......................... 702/27; 702/32; 395/500.33
[58] Field of Search .................................. 364/496, 497, 364/498, 499, 578; 395/23, 21, 22, 24, 920, 924; 382/101, 102, 155, 156, 159, 160, 161, 182, 187, 188, 216

[56] References Cited

U.S. PATENT DOCUMENTS

| | | | |
|---|---|---|---|
| 5,025,388 | 6/1991 | Cramer, III et al. | 364/496 |
| 5,113,483 | 5/1992 | Keeler et al. | 395/23 |
| 5,167,009 | 11/1992 | Skeirik | 395/27 |
| 5,260,882 | 11/1993 | Blanco et al. | 364/499 |
| 5,265,030 | 11/1993 | Skolnick et al. | 364/496 |
| 5,271,068 | 12/1993 | Ueda et al. | 382/216 |
| 5,276,771 | 1/1994 | Manukian et al. | 395/24 |
| 5,384,895 | 1/1995 | Rogers et al. | 395/23 |
| 5,526,281 | 6/1996 | Chapman et al. | 364/496 |
| 5,555,317 | 9/1996 | Anderson | 382/159 |
| 5,636,291 | 6/1997 | Bellegarda et al. | 382/187 |
| 5,638,491 | 6/1997 | Moed | 395/23 |

OTHER PUBLICATIONS

Andrea, et al., "Applications of Neural Networks in Quantitative Structure–Activity Relationship of Dihydrofolate Reductase Inhibitors," Journal of Medicinal Chemistry, vol. 34, No. 9, 1991, pp. 2824–2836.

Aoyama, et al., "Neural Networks Applied to Quantitative Structure Activity Relationship Analysis," Journal of Medicinal Chemistry, 1990, vol. 33, No. 9, pp. 2583–2590.

(List continued on next page.)

*Primary Examiner*—Melanie A. Kemper
*Attorney, Agent, or Firm*—Swernofsky Law Group

[57] ABSTRACT

Explicit representation of molecular shape of molecules is combined with neural network learning methods to provide models with high predictive ability that generalize to different chemical classes where structurally diverse molecules exhibiting similar surface characteristics are treated as similar. A new machine-learning methodology is disclosed that can accept multiple representations of objects and construct models that predict characteristics of those objects. An extension of this methodology can be applied in cases where the representations of the objects are determined by a set of adjustable parameters. An iterative process applies intermediate models to generate new representations of the objects by adjusting said parameters and repeatedly. retrains the models to obtain better predictive models. This method can be applied to molecules because each molecule can have many orientations and conformations (representations) that are determined by a set of translation, rotation and torsion angle parameters.

32 Claims, 15 Drawing Sheets

OTHER PUBLICATIONS

Aoyama, et al., "Obtaining the Correlation Indices Between Drug Activity and Structural Parameters Using a Neural Network," Chemical Pharmaceutical Bulletin, vol. 39, No. 2, 1991, pp. 372–378.

Blankley, "Introduction: A Review of QSAR Methodology," Academic Press, Inc. (1983), pp. 1–17.

Boulu, et al., "Voronoi Binding Site Model of a Polycyclic Aromatic Hydrocarbon Binding Protein," J. Med. Chem. (1990) vol. 33, pp. 771–775.

Boulu, et al., "Voronoi Binding Site Models: Calculation of Binding Modes and Influence of Drug Binding Data Accuracy," Journal Of Computational Chemistry (1989) vol. 10, No. 5, pp. 673–682.

Cramer III, et al., "Comparative Molecular Field Analysis (COMFA)," J. Am. Chem. Soc., vol. 110, No. 18 (1988) pp. 5959–5967.

Crippen, "Voronoi Binding Site Models," Journal of Computational Chemistry (1987) vol. 8, No. 7, pp. 943–955.

Crippen, "Deduction of Binding Site Structure From Ligand Binding Data," Annals of the New York Academy of Sciences (1984) vol. 439, pp. 1–11.

Crippen, et al., "Distance Geometry and Molecular Confirmation," Research Studies Press Ltd., 8. Ligand Binding, pp. 361–429, No date.

Doweyko, "The Hypothetical Active Site Lattice: An Approach To Modelling Active Sites from Data on Inhibitor Molecules," Journal of American Chemistry (1988) vol. 31, No. 7, pp. 1396–1406.

Ghose, et al., "Use of Physicochemical Parameters in Distance Geometry and Related Three–Dimensional Quantitative Structure–Activity Relationships: A Demonstration Using *Escherichia coli* Dihydrofolate Reductase Inhibitors," Journal of Medicinal Chemistry, vol. 28, No. 3, 1985, pp. 333–346.

Good, et al., "Structure–Activity Relationships from Molecular Similarity Matrices," Journal of Medicinal Chemistry, vol. 36, No. 4, Feb. 19, 1993, pp. 433–438.

Hopfinger, "A QSAR Investigation of Dihydrofolate Reductase Inhibitors by Baker Triazines Based Upon Molecular Shape Analysis," J. Am. Chem. Soc. (1980) vol. 102, pp. 7196–7206.

Nicklaus, et al., "QSAR of Conformationally Flexible Molecules: Comparative Molecular Field Analysis of Protein–Tyrosine Kinase Inhibitors," Journal of Computer–Aided Molecular Design (1992) vol. 6, pp. 487–504.

Oinuma, et al., "Neural Networks Applied to Structure–Activity Relationships," Journal of Medicinal Chemistry, vol. 33, No. 3, 1990, pp. 905–908.

Simon, et al., "Mapping of Dihydrofolate–Reductase Receptor Site by Correlation with Minimal Topological (Steric) Differences," J. Theor. Biol. (1977), vol. 66, pp. 485–495.

Smellie, et al., "Fast Drug–Receptor Mapping by Site–Directed Distances: A Novel Method of Predicting New Pharmacological Leads," J. Chem. Inf. Comput. Sci., vol. 31, No. 3 (1991) p. 386–392.

Viswanadhan, et al., "Mapping the Binding Site of the Nucleoside Transporter Protein: A 3D–QSAR Study," Biochemica et Biophysica Acta., 1039 (1990) pp. 356–366.

[a', b', c', d', e', ...]

[a, b, c, d, ...]

INCLUDED: MOL 1, MOL 2₂
EXCLUDED: MOL 2₁, MOL 3, MOL 4

Training molecule 3: observed with *low activity*, hard-box hypothesis *should predict* low activity Initial pose: Predicted LOW Generalization Procedure produces consistent hypothesis *even when re-posing*

Modified pose: Predicted LOW

Final pose: Predicted LOW

Training molecule 4: observed with *low activity*, hard-box hypothesis *should predict* low activity Initial pose: Predicted LOW Generalization Procedure produces consistent hypothesis *even when re-posing*

Modified pose: Predicted LOW

Final pose: Predicted HIGH
Hypothesis fails!

INACTIVE

ACTIVE

ACTIVE

ACTIVE

INACTIVE

INACTIVE

MACHINE-LEARNING APPROACH TO MODELING BIOLOGICAL ACTIVITY FOR MOLECULAR DESIGN AND TO MODELING OTHER CHARACTERISTICS

This application is a continuation-in-part of application Ser. No. 08/066,389, filed May 21, 1993, now abandonded in the name of the same inventors, with the same title, and assigned to the same assignee. This is a 371 of PCT/U.S. Ser. No. 94/05877 filed on May 20, 1994.

BACKGROUND OF THE INVENTION

This invention relates in general to a machine-learning approach to modeling biological activities or other characteristics and, in particular, to a machine-learning approach to modeling biological activity for molecular design or other characteristics. In modeling biological activity, the approach is preferably shaped-based.

The shape that a molecule adopts when bound to a biological target, the bioactive shape, is an essential component of its biological activity. This shape, and any specific interactions such as hydrogen bonds, can be exploited to derive predictive models used in rational drug design. These can be used to optimize lead compounds, design de novo compounds, and search databases of existing compounds for novel structures possessing the desired biological activity. In order to aid the drug discovery process, these models must make useful predictions, relate chemical substructures to activity, and confidently extrapolate to chemical classes beyond those used for model derivation.

Physical data such as x-ray crystal structures of drug-target complexes provide a shape model directly and have led to recent successes in structure-based drug-design. However, in the absence of such data, rational drug design must rely upon predictive models derived solely from observed biological activity. Several methods exist that produce predictive models relying, in part, on molecular shape.

Existing methods for constructing predictive models are unable to model steric interactions accurately, particularly when these interactions involve large regions of the molecular surface. Existing quantitative structure-activity relationship (QSAR) models are severely limited by the types of molecular properties they consider. Methods that employ properties of substituents assume that the molecules share a common structural skeleton, and hence cannot be extrapolated to molecules with different skeletons. Many methods employ ad hoc features that make it difficult to interpret the models as a guide for drug design. Pharmacophore models (e.g., BioCAD) model activity in terms of the positions of a small number of atoms of functional groups. This overcomes many of the problems of traditional QSAR methods, but it has difficulty addressing steric interactions.

In U.S. Pat. No. 5,025,388 to Cramer, III, et al., a comparative molecular field analysis (COMFA) methodology is proposed. In this methodology, the three-dimensional structure for each molecule is placed within a three-dimensional lattice and a probe atom is chosen, placed successively at each lattice intersection, and the steric and electrostatic interaction energies between the probe atom and the molecule calculated for all lattice intersections. Such energies are listed in a 3D-QSAR table. A field fit procedure is applied by choosing the molecule with the greatest biological activity as the reference in conforming the remaining molecules to it. In determining which conformation of the molecule to use in the analysis, COMFA proposes using averaging or Boltzman distribution weighting to determine a most representative conformer. After the 3D-QSAR table is formed, a partial least squares analysis and cross-validation are performed. The outcome is a set of values of coefficients, one for each column in the data table, which when used in a linear equation relating column values to measured biological values, would tend to predict the observed biological properties in terms of differences in the energy fields among the molecules in the data set, at every one of the sampled lattice points.

The COMFA method is disadvantageous since it requires that the chemist guess the alignment and active conformation of each molecule or, alternatively, compute the average or a weighted distribution of the steric and electrostatic fields for all conformations. This can undermine the applicability and accuracy of the method.

The COMFA method is also disadvantageous because it constructs a linear model to predict activity as a function of the properties measured at the grid points. Biological activity is an inherently non-linear function of molecular surface properties (such as electrostatic, weak polar, and van der waals interactions). In COMFA these nonlinearities must be captured in the field values measured at the grid points.

None of the above-described approaches is entirely satisfactory. It is therefore desirable to provide an improved approach for modeling biological activity in which the above-described difficulties are alleviated.

SUMMARY OF THE INVENTION

The invention provides a method of predicting activities of molecules in response to data from actual assays of a set of training molecules. In a preferred embodiment, this method includes selecting initial conformations and orientations ("poses") for molecules in a training set, constructing a model in response to those poses, and revising the model by altering parameters and by selecting new poses in response to differences between the model and data from actual assays.

An important advantage of the approach of this application over COMFA is that a non-linear mathematical model is employed. This permits a surface representation that is easier to understand and more efficient to compute. The non-linearity is handled by a mathematical model.

This invention is based on the observation that it is difficult for a scientist to provide good guesses about the best bioactive pose for each molecule and that it is desirable to provide a method where the model can be refined to generate new molecular orientations and conformations even though the initial guesses may be mediocre. This invention is also based on the observation that almost all of the chemical interactions between molecules of interest to biochemistry and medicinal chemistry are based entirely on surface interactions so that the predictive model would best utilize a surface-based representation of molecular shape.

One aspect of the invention is directed towards an iterative process that produces better models. In many binding interactions between molecules, not all of the characteristics of the molecule considered are of equal importance. Using a modeling approach permits the user to focus on the salient features of the molecules. This aspect of the invention is directed towards a method for predicting activity of molecules with respect to a chemical function based on known activities of a plurality of molecules. Each molecule has one or more conformations and orientations, and each combination of a conformation and an orientation defines a pose of a molecule. The method comprises selecting one or more poses from possible poses of each molecule as the initial poses of a training set. A model is then constructed with model parameters for predicting activity of poses with respect to said chemical function and model parameter values are then set. The activities of at least some of the initial poses in the training set are predicted using the model and the model parameter values. The predicted activities of at least some of the initial poses of molecules are then compared to the known activities of such molecules. The model parameter values are then modified based on a prior comparison between predicted activities of poses in the set and their known activities to minimize the differences between the predicted activities of said at least some of the poses of molecules in the set and the known activities of such molecules. The poses of the molecules are also modified or re-selected so as to obtain an updated training set of enhanced poses with higher predictive value than poses in the set prior to the modifying step. The model and modified model parameter values are then used to predict the activity of additional molecules whose activity is unknown.

In the preferred embodiment, the model parameter values and poses are modified iteratively until the model parameter values as well as the poses both converge before the model and the modified model parameter values are used to predict the activity of the molecules whose activity is unknown. For each molecule, the pose having the highest predicted activity is the best pose of the molecule. Preferably, the model parameter values are modified based on a prior comparison between predicted activities of only the best pose or poses for each molecule in the set and their known activities.

Another aspect of the invention is directed toward a shape-based approach to modeling biological activity. This aspect is directed towards a method for predicting activity of molecules with respect to a chemical function based on known activities of a training set of molecules. Each molecule in the set has one or more poses as defined above. The method comprises extracting a set of feature values from each of the poses of molecules in the training set, said feature values related to said activity. The extracting step includes the following two steps: creating a surface representation of each of the poses of each of the molecules in the training set and obtaining a feature value between at least one sampling point and a point on the surface representation of each of the poses. A model is then constructed for predicting activity of poses with respect to the chemical function using the feature values and the model is then used to predict the activity of a molecule not in the training set. In the preferred embodiment, the feature value is obtained by determining the minimum distance between said at least one point and the surface representations of the poses.

Yet another aspect of the invention is directed towards a general machine-learning method for predicting Characteristics of an object based on known characteristics of a plurality of other objects. Each object has one or more representations. The method comprises selecting one or more representations from possible representations of each of the other objects as the initial representations, constructing a model for predicting characteristics of the representations, and predicting the characteristics of at least some of the initial representations using the model and comparing the predicted characteristics of initial representations of the other objects to their known characteristics. For each of the other objects, the representation that has better characteristics than other representations of the same object defines the best representation of the object. The method further comprises modifying the model based on a prior comparison between predicted characteristics of the best representations of the other objects and their known characteristics to minimize the differences between the predicted characteristics of said best representations of the other objects and their known characteristics. The last step involves using the modified model to predict characteristics of an object not in the training set.

In another aspect, the invention provides a method of classifying objects into one of a plurality of categories, in response to example objects from those categories. In a preferred embodiment, this method includes selecting initial exemplars ("poses") for those categories, constructing a model in response to those poses, and revising the model by altering parameters and by selecting new poses in response to differences between the model and data from actual classification of new objects into those categories. Objects may be written characters and categories may be known letters or symbols. Objects may be speech fragments and categories may be linguistic units such as consonants, vowels, syllables or words. Objects may be pictures and categories may be known physical images.

GENERAL DESCRIPTION OF THE PREFERRED EMBODIMENT

A novel modeling approach is proposed using a surface-based representation of molecular shape that employs neural network learning techniques to derive robust predictive models. Trained models predict the bioactive shape of molecules and can be readily interpreted to guide the design of new active compounds. The method is demonstrated on musk odor perception, a problem believed to be determined by subtle steric interactions.

This approach combines three advances: a representation that characterizes surface shape such that structurally diverse molecules exhibiting similar surface characteristics are treated as similar; a new machine learning methodology that can accept multiple orientations and conformations of both active and inactive molecules; and an iterative process that applies intermediate models to generate new molecular orientations to produce better predictive models. The method is first outlined, then predictive results are presented, and lastly the details of the method are described.

The procedure begins by conducting a search for low energy conformations of the training molecules. This provides a pool of energetically accessible shapes for each molecule. They are then placed into a set of initial orientations that coarsely align the gross shape and electrostatically important regions of the molecules. From these starting poses, we extract feature values using either the point-based or ray-based feature extraction method. These feature values (along with the known activities of the corresponding molecules) are then provided as input to a neural network, which is trained to construct an initial model of activity. To improve predictive performance, we apply the learned model to automatically compute additional discriminative molecular poses. The model is refined using the new poses, and the process iterates until it converges on a best model and a best pose for each molecule. Activity predictions for new molecules are then obtained by applying the final model. As in the training process, the model automatically computes the best conformation and orientation for each molecule—the predicted bioactive pose. It can be visualized in three dimensions to identify required, allowed and disallowed regions of space around a candidate molecule.

DETAILED DESCRIPTION OF THE PREFERRED EMBODIMENT

Figure 1:
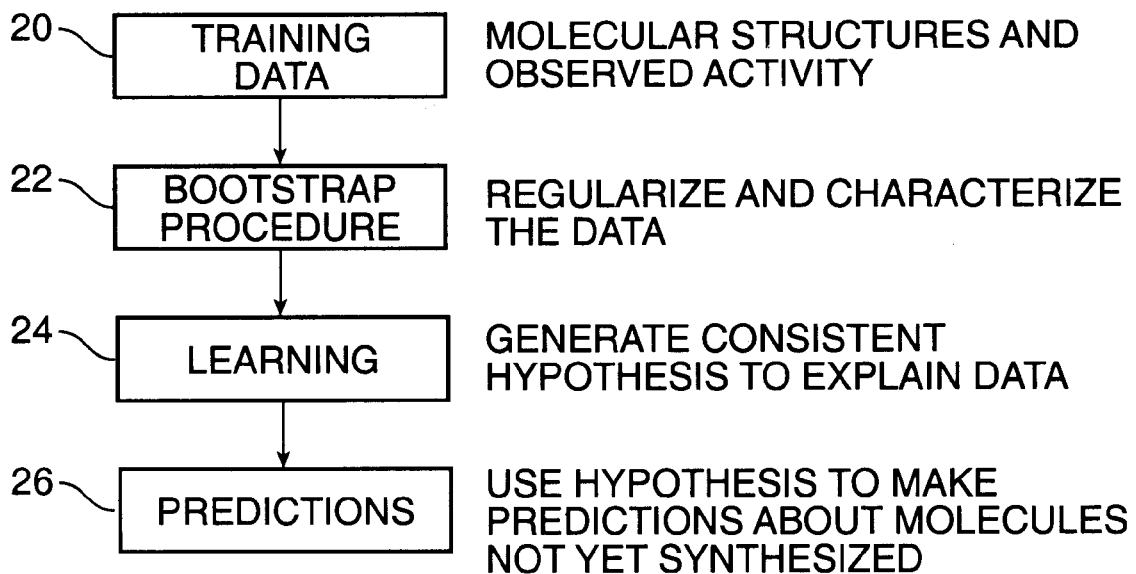
FIG. 1 is a flow diagram of a molecular shape learning system to illustrate the invention.
Figure 2:
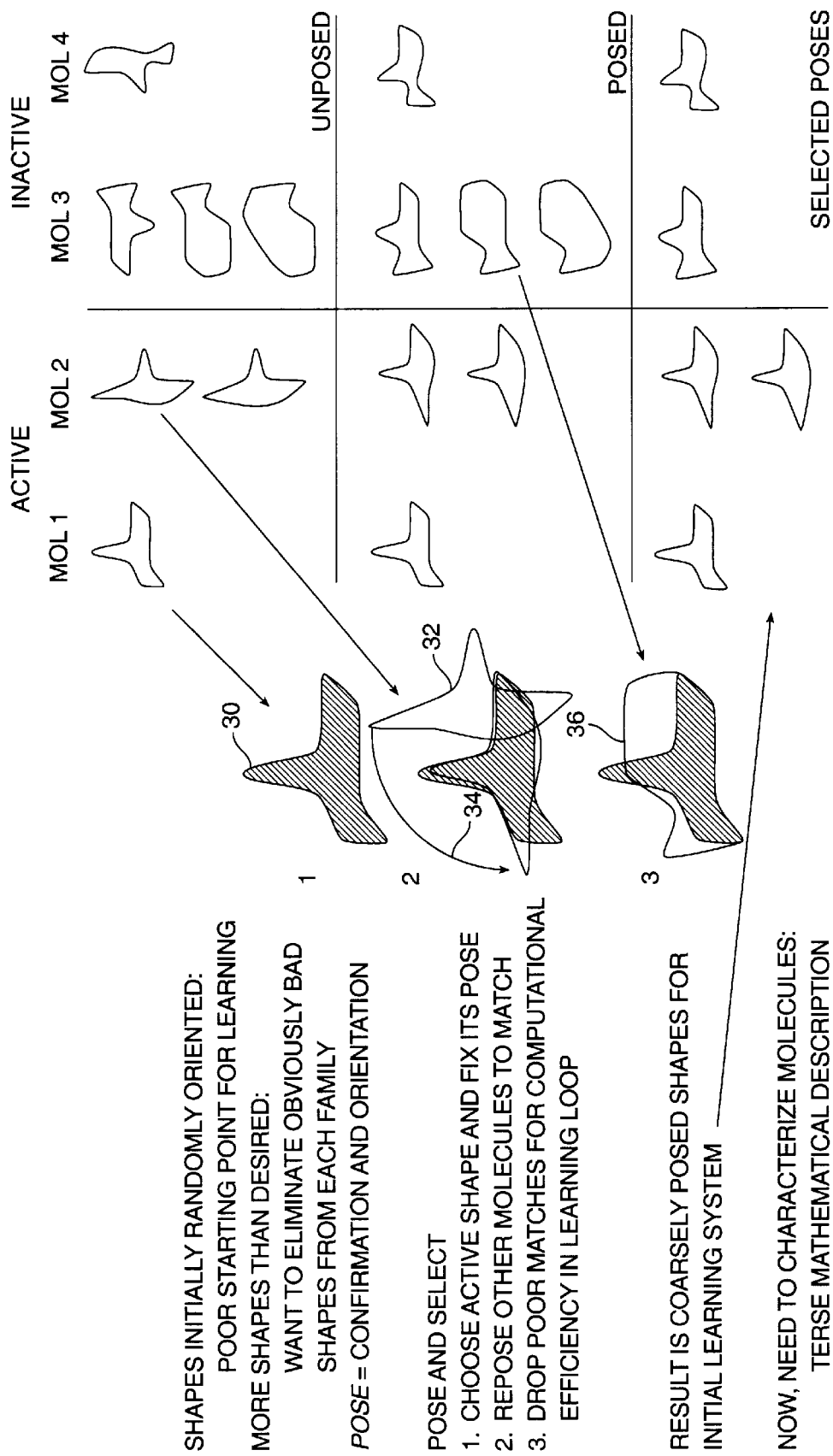
FIG. 2 is a schematic illustration of four different molecules, each with one or more different orientations and conformations or poses to illustrate the bootstrap procedure of FIG. 1.

The invention will now be described in detail by reference to figures. FIG. 1 is a flow chart showing the overall structure of the system. In order to predict the activity of molecules not yet synthesized or for which not much is known with respect to a particular chemical function, such as binding to a particular receptor, one would first start with molecular structures and assay values of known molecules with known activities with respect to such chemical function. This is accomplished in the first step 20 in FIG. 1 by gathering the training data. Such data is subsequently used in a learning model which is refined to generate consistent hypotheses to explain the training data. However, in order to make the learning process more efficient, it is desirable to employ a bootstrap procedure 22. This procedure is illustrated in FIG. 2 in three steps: finding the conformers, posing the conformers and selecting initial poses from the poses to form an initial training set. After the training set is formed, the set is used in a learning step 24 to refine a system which is then used to predict (26) the activity of a molecule not in the training set.

As shown in FIG. 2, the training data includes data on four different molecules, where molecules 1 and 2 are active with respect to a particular chemical function and molecules 3 and 4 are inactive with respect to such function. As known to those skilled in the art, biologically active molecules can take on different shapes known as conformers or conformations defined by the internal torsion angles of the rotatable bonds in the molecule. As shown in FIG. 2, molecules 1 and 4 each have only one conformer, molecule 2 two conformers and molecule 3 three conformers. In order to increase the computational efficiency in learning, it is desirable to choose only the conformations that are best in confirming or refuting the learning model.

The first step in this selection involves posing the molecule. A pose of a molecule is defined by its conformation (internal torsion angles of the rotatable bonds) and orientation (three rigid rotations and translations). This mathematically defines the pose of the molecule. First, a conformer of an active molecule is chosen and its pose is first fixed. As shown in FIG. 2, molecule 1 is chosen and its pose 30 is fixed. Then the conformers of the other molecules are realigned to match pose 30, such as in the realignment of conformer 32 along arrow 34. Conformer 36 of molecule 3 is moved along all three dimensions until it overlaps as much as possible pose 30 as shown in FIG. 2. In chemical terms, this is analogous to permitting the molecule to rotate, translate and alter its conformation to achieve its best possible fit to the binding site. The rotation, translation and alteration in the internal torsion angles of the rotatable bonds in a molecule is referred to herein as reposing of the molecule.

In other words, since the fixed pose of molecule 1 known to have high activity is used as the reference for reposing the remaining molecules, this crudely simulates the process of reposing the other molecules to achieve the best possible fit to the binding site. The reposed conformers of molecules 2, 3 and 4 are shown in FIG. 2 in the category labeled "posed". The above-described process can be performed using a number of software packages available commercially, such as Catalyst from BioCAD, Foster City, Calif., and Batchmin available from Columbia University, New York City, N.Y.

The learning process 24 now begins with a selection of only some of the poses to be in the training set. In other words, poor matches are dropped for computational efficiency in the subsequent learning process. For example, two of the poses of molecule 3 have been dropped to arrive at a training set of five selected poses as shown in FIG. 2. In making the selection, various properties of the four molecules known to chemists may be used, including physical and chemical properties such as shape, electrostatic interaction, salvation and biophysical properties.

Before the selected poses may be used for training, the relevant features of these poses are first extracted. The COMFA methodology described in U.S. Pat. No. 5,025,388, for example, employs a three-dimensional lattice structure and extracts the relevant features by calculating the steric and electrostatic interaction energies between a probe atom placed at each of the lattice intersections and the molecule. As indicated above, the receptor site in a binding interaction "sees" only the surfaces and not the interior of a molecule. By choosing a three-dimensional lattice and modeling the learning process based on the interaction energies between these lattice points and the molecule, the COMFA methodology has failed to focus in on the critical portion of the molecule, namely its surface. Consequently, extraneous data not particularly relevant to binding interactions may be included and may compromise the subsequent learning process and cause it to give incorrect weight to critical surface features. The feature extraction methods of this invention overcome such defects.

Surface Representation

Figure 3:
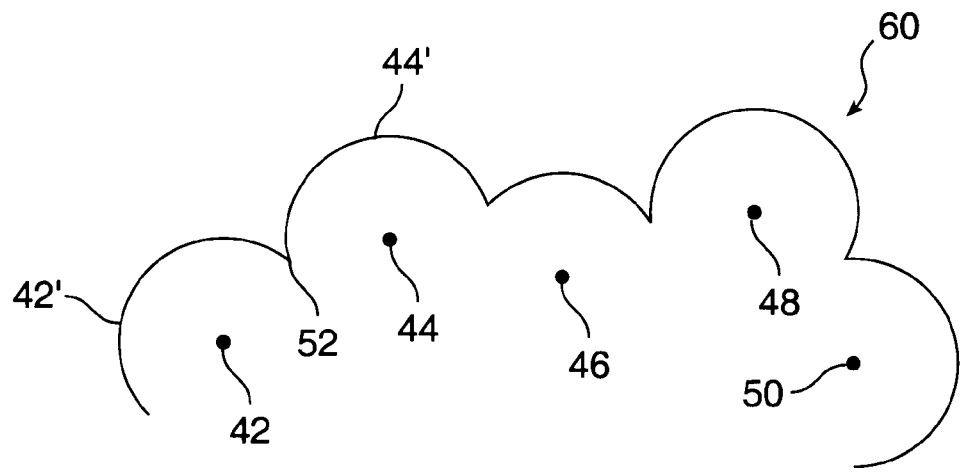
FIG. 3 is a schematic view of the van der Waals surface representations of atoms on a surface of a pose.

This invention envisions creating a surface representation of each of the poses and then obtaining a feature value between at least one sampling point and a point on the surface representation of each of the poses. FIG. 3 is a schematic illustration of a portion of a surface of a molecule with five atoms whose nuclei are at 42–50 at such surface portion. The van der Waals surface of each of the five atoms is first found. The van der Waals surfaces of adjacent atoms would intersect; thus, the van der Waals surface 42' of atom with nucleus at 42 intersects surface 44' of atom with nucleus at 44 at ridge 52. The portions of surfaces 42', 44' that extend outwards from ridge 52 are then taken as a surface representation of the molecule around atoms with nuclei at 42 and 44. Thus, the curved surface 60, having a number of ridges such as ridge 52 at the intersections of adjacent van der Waals surfaces, is a surface representation of the portion of the molecule shown in FIG. 3.

As known to those skilled in the art, the electron density around each atom can be represented as a Gaussian function of distance from the nucleus of the atom where the peak of such Gaussians would more or less coincide with the van der Waals radius of the atom. A surface representation of the portion of the molecule shown in FIG. 3 can then be obtained by summing the Gaussian functions for all the five atoms with nuclei at 42–50 where the sum function also has a peak surface that would more or less coincide with surface 60. The surface representation arrived at using the van der Waals surfaces of the atom has been found to be adequate and easy to find for most purposes for modeling biological and chemical activity whereas the sum of the Gaussian approach gives a scientifically more rigorous representation of such surface. The details of finding the van der Waals surfaces of atoms and calculations involving a surface such as surface 60 are known to those skilled in the art and will not be explained in detail here; although an improved method of calculating the minimum distance between such surface and a sampling point is discussed below. Similarly, the Gaussian distributions for the atoms and method for summing them are also known to those skilled in the art and will not be explained in detail here. Other than van der Waals and Gaussian surface representations, other types of surface representation are possible, such as a Connolly surface. See, M. J. Connolly, *J. Appl. Cryst.*, 16, 548 (1983).

Feature Extraction

The feature values, including steric, electrostatic or other feature values may be extracted by first specifying at least one sampling point and then obtaining a feature value between such sampling point and a point on the surface representation of each of the poses. In the preferred embodiment, the point is outside but near the molecular surface and the feature value is extracted by determining, for example, the minimum distance between such sampling point and the surface representation of the pose. For simplicity, a surface representation of a pose determined in the manner above will be referred to simply as the surface of the pose. An electrostatic feature value may be extracted as the electrostatic interaction between a probe atom placed at such sampling point and the pose. Alternatively, the electrostatic feature value may be the sum of the Coulomb force interactions between the probe atom and atoms of the pose surface. The above-described approach will be referred to herein as the point-based feature extraction approach. Preferably, a number of sampling points are chosen surrounding the poses. In other words, the same sampling points are used to extract features from each of the poses in the training set. To arrive at a common set of sampling points, one may select the points by reference to the averaged position of the poses in the training set.

Figure 4:
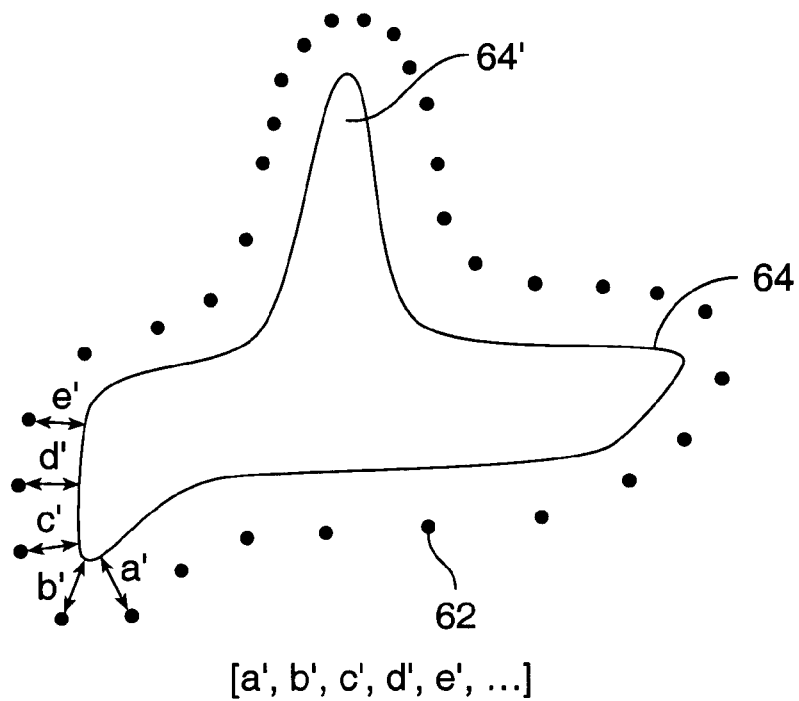
FIG. 4 is a schematic illustration of a pose of a molecule and a number of points around the surface representation to illustrate a point based system for feature extraction.

FIG. 4 is a schematic illustration of a number of sampling points 62 surrounding the surface of a pose 64, which may be an averaged position of the poses in the set. If the fine features of portion 64' of the pose are deemed to be particularly important for the activity of the pose, the density of sampling points 62 may be increased surrounding such portion as illustrated in FIG. 4. Point based feature extraction has the advantage that the feature values (minimum distances, electrostatic interaction, . . . ) will not change abruptly upon changing the orientation or conformation of the pose. Also, when differentiability of the feature values with respect to orientation and conformational parameters is important, point based feature extraction gives rise to feature values which are differentiable functions of the orientation and conformational parameters. The steric feature values may simply comprise the minimum distance between each of the sampling points and the surface representation of the molecule, such as a', b', c', d', e' as shown in FIG. 4. The electrostatic feature values may comprise the electrostatic interaction energies or sums of Coulomb forces between a probe atom placed at each of the sampling points and the molecule. Other feature values may be extracted in a similar manner.

Figure 5A:
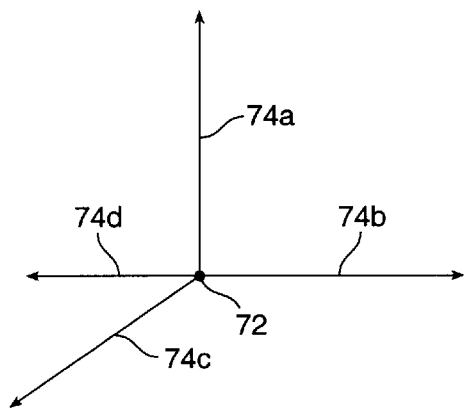
FIG. 5A is a schematic view of a ray-based feature extraction system to illustrate the invention.
Figure 5B:
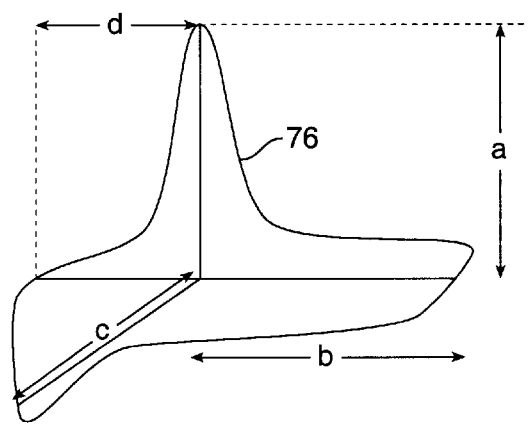
FIG. 5B is a schematic view of a pose of a molecule and a ray-based feature extraction system to illustrate such system.
Figure 5C:
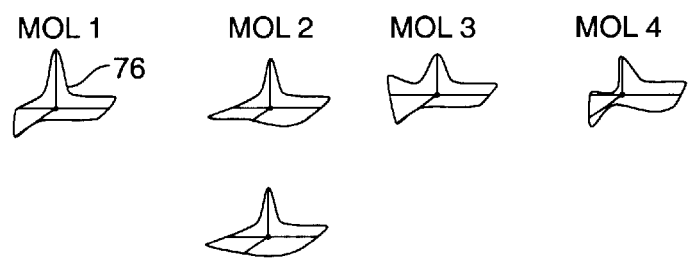
FIG. 5C is a schematic view of one or more poses of four different molecules to illustrate the ray-based feature extraction system.

Another possible feature extraction method is a ray-based method as illustrated in FIGS. 5A–5C. In ray-based feature extraction, first one or more points are chosen, such as point 72, preferably located inside the molecular surface, and a number of rays with fixed directions are chosen, such as rays 74a, 74b, 74c, 74d diverging from point 72. The points at which the surface representation of the molecule intersects these rays would yield the steric feature values a, b, c, d as illustrated in FIG. 5B. Thus, the four rays intersecting the surface of pose 76 intersect the pose surface at distances a, b, c, d from point 72 so that the set of feature values representing pose 76 is [a, b, c, d, . . . ]; a, b, c, d being the steric feature values. As shown in FIGS. 5B, 5C, pose 76 of molecule 1 has feature values [a, b, c, d, . . . ]. The two poses of molecule 2 and the single pose of each of molecules 3 and 4 each has a set of feature values representing it as illustrated in FIG. 5C.

Feature Point Placement

Figure 15:
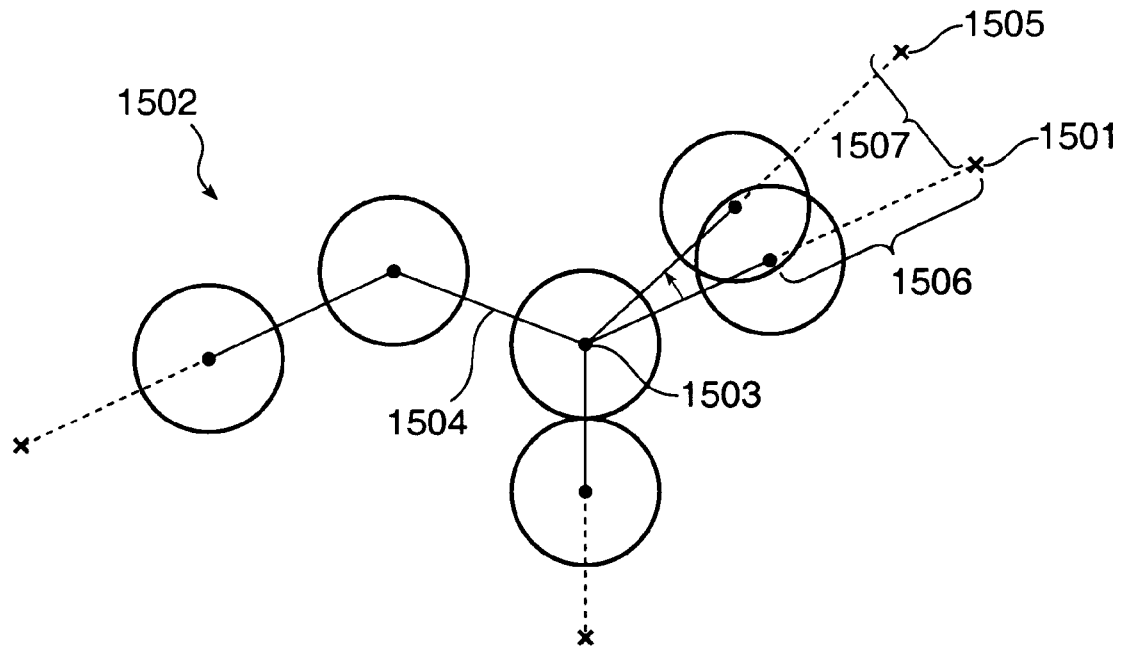
FIG. 15 shows a set of feature points used in a method of point placement.

FIG. 15 shows a set of feature points used in a method of point placement.

In a preferred embodiment, a set of feature points 1501 may be selected with reference to the selected pose of the molecule 1502. The molecule 1502 is represented as an nondirected graph, where the atoms 1503 of the molecule are points of the graph and where the bonds 1504 between atoms are vertices of the graph. A set of terminal atoms 1503 (ignoring hydrogen atoms) are selected by examination of the molecule 1502.

For each terminal atom 1503, a potential feature point 1505 is placed in line with the bond 1504 associated with that terminal atom 1503. The potential feature point 1505 is placed a selected distance 1506 (preferably 2 angstroms) away from the terminal atom 1503 along the line of the bond 1504. The selected distance 1506 is selected by analogy to the mean diameter of a carbon atom, and may be selected to be a different distance in response to the chemistry of the set of molecules 1502 under investigation. In a preferred embodiment, the $\mu$ parameter is initialized to the same value as the selected distance 1506.

A set of feature points 1501 is selected as follows: Each new molecule 1502 is selected in turn. For each molecule 1502, each pose of that molecule 1502 is selected in turn. For each pose, each terminal atom 1503 is selected in turn. For each terminal atom 1503, the potential feature point 1505 is placed.

If the potential feature point 1505 is less than a selected distance 1507 (preferably 2 angstroms) away from a nearest feature point 1501 already selected, the potential feature point 1505 is not selected. Otherwise, the potential feature point 1505 is added to the set of selected feature points 1501. In the case where no feature points 1501 have been selected yet, the first potential feature point 1505 is always distance 1507 is selected by analogy to the mean diameter of a carbon atom, and may be selected to be a different distance in response to the chemistry of the set of molecules 1502 under investigation. A preferred number of feature points 1501 is about 200 to about 600.

It would be clear to those skilled in the art, after perusal of this application, that feature points 1501 could be selected from the set of potential feature points 1505 in other ways, including (a) selection of feature points 1505 to represent clusters of potential feature points 1505, or (b) selection of feature points 1505 to completely span the set of potential feature points 1505 without being closer than the selected distance 1507. It would also be clear to those skilled in the art, after perusal of this application, that such other ways would be workable within the context of this application, and are within the scope and spirit of the invention.

Polar Features

Figure 16:
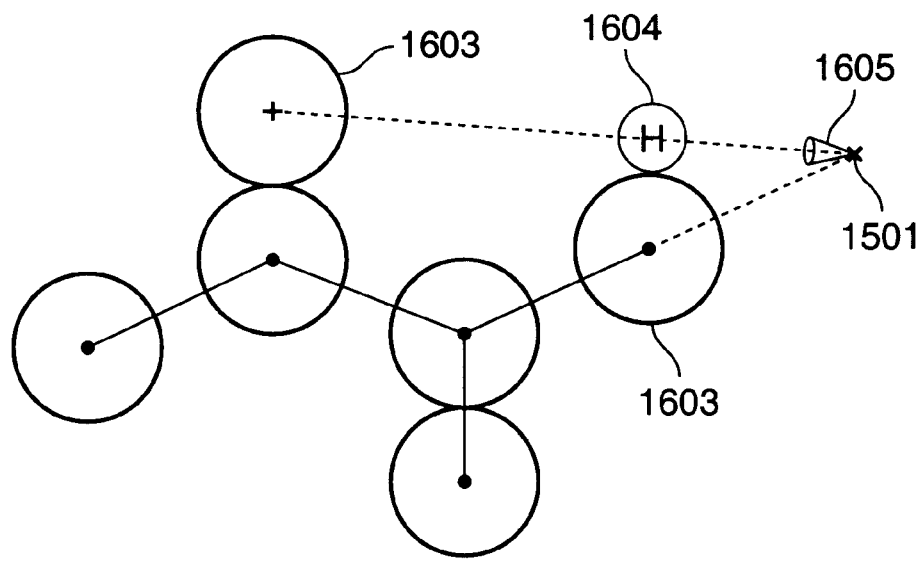
FIG. 16 shows determination of a feature relating to a polar atom.

FIG. 16 shows determination of a feature relating to a polar atom.

In a preferred embodiment, a selected feature includes the distance 1601 from a feature point 1501 to the center of a feature atom 1602. The feature atom 1602 is selected to be a polar atom with a selected sign (i.e., an electron acceptor atom having a positive sign, or an electron donor atom having a negative sign), other than a hydrogen atom 1604. Where there are polar atoms of opposite sign, nonpolar atoms 1603, or hydrogen atoms 1604 between the feature point 1501 and the feature atom 1602, the presence of those other atoms is not used in computing the distance from the feature point 1501 to the feature atom 1602.

In a preferred embodiment, a distance 1601 from the feature point 1501 to the center of the feature atom 1602 is determined, but this distance 1601 may be adjusted in response to the size of the feature atom 1602, if the size of the feature atom 1602 is greatly different from that of a carbon atom. The feature may also be adjusted in response to an estimated hydrogen bonding strength of the feature atom 1602, e.g., by hydrogen bonding strength. An additional feature may also be determined relating to an angular direction 1605 from the feature point 1501 to the feature atom 1602.

Initial Molecule Alianment

Figure 17:
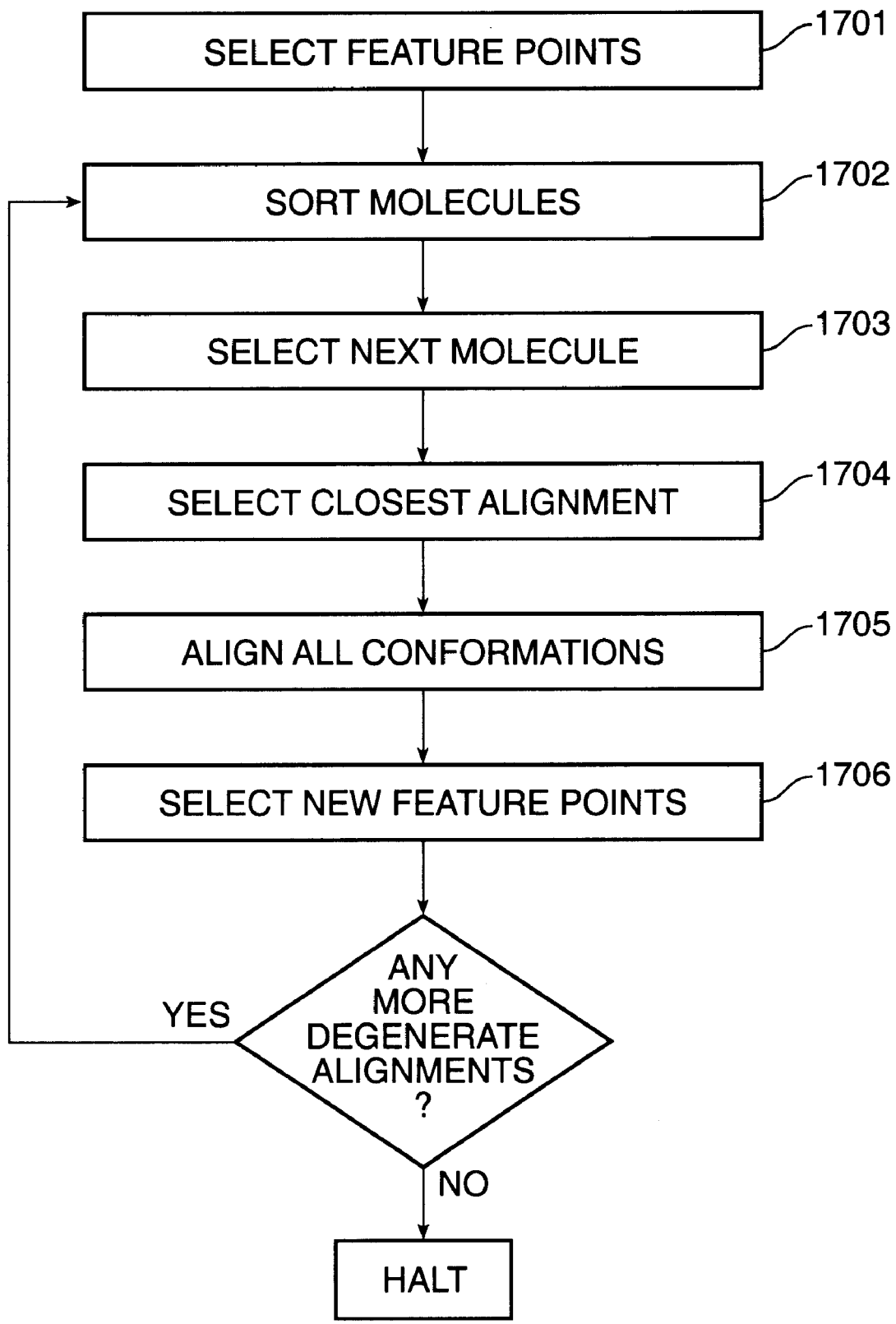
FIG. 17 shows a method of initial molecule alignment.

FIG. 17 shows a method of initial molecule alignment.

In a preferred embodiment, when two molecules each have multiple poses, it is generally desirable to initially align the molecules with each other so that predicted activity for a first molecule is best related to predicted activity for a second molecule.

At a step 1701, feature points 1501 are selected.

At a step 1702, the set of training molecules is sorted by activity.

At a step 1703, a pose for the next molecule having the greatest activity is selected for alignment. The alignment of the first molecule is presumed to be already selected, so on the first execution of this step, the second molecule is selected for alignment.

At a step 1704, a lowest energy conformation of the selected molecule is aligned with each previous molecule (i.e., each molecule that has greater activity). This step is performed as follows:

A set of parameters for alignment of the molecule are determined. A distance metric is determined between the selected molecule and each previous molecule, equal to the sum of absolute values of differences between feature values. A minimization procedure (such as gradient descent or simulated annealing) is performed to alter the parameters to minimize the distance metric to below a selected threshold $\partial$. Once the distance metric falls below $\partial$, no further minimization is performed.

At a step 1705, the previous molecule that has a smallest distance from the selected alignment of the selected molecule is determined. All conformations of the selected molecule are aligned to this previous molecule.

At a step 1706, a new set of feature points 1501 are selected in response to the new alignments of all molecules.

At a step 1707, it is determined if there are any degenerate alignments remaining. If not, the alignment process is halted. Otherwise, the process continues with step 1702.

Form of the Model

Once features have been extracted for each initial pose in the initial training set, these features are input to a parameterized mathematical model (neural network) to produce an activity prediction. Let V (M, P) be the vector of n features extracted to represent molecule M in pose P. Let the kth component of this vector be denoted V (M, P)$_k$.

During training, the optimal values for the model parameters are determined. It will be understood that the scope of this invention includes a wide range of mathematical models, including linear models and nonlinear models. In the preferred embodiment, the model has the form:

$$\text{Activity } (V(M, P)) = \text{Sigmoid} \left[ \sum_{j=1}^{m} U_j F_j(V_j, V(M, P), \mu, \sigma) \right] \quad (1)$$

where m is the number of weights sigmoid $(X)=1/(1+\exp(-x))$ exp is the exponential function (whose base e is the base of the natural logarithm)

$U_j$ is a real-valued weight and $$F_j(V_j, V(M, P), \mu, \sigma) = \text{Sigmoid}\left[\sum_{i=1}^{n} V_{ji} G(V(M, P)_i, \mu_i, \sigma_i)\right] \quad (2)$$

$$G(V(M, P)_i, \mu_i, \sigma_i) = \exp\left[-\frac{(V(M, P)_i - \mu_i)^2}{2\sigma_i^2}\right]$$

Figure 6A:
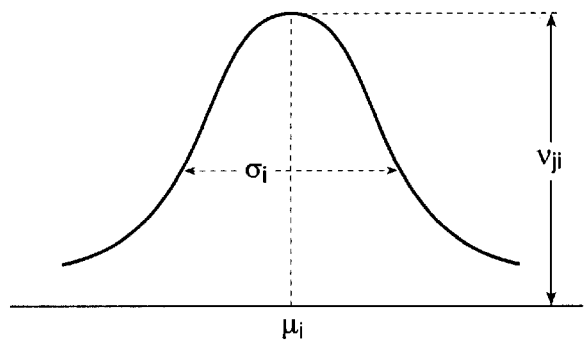
FIG. 6A is a graphical illustration of a Gaussian function to illustrate the invention.

$\mu_i$ is a real-valued location parameter
$\sigma_i$ is a real-valued width parameter
The parameters of this model are:
  $u_j$ (j=1. . . n)
  $v_{ji}$ (j=1. . . n, i=1. . . m)
  $\mu_i$ (i=1. . . m)
  $\sigma_i$ (i=1. . . m).
  n In this embodiment, the function G is a Gaussian-like function that will produce large values when the measured feature $V(M, P)_i$ is near to $\mu_i$ and smaller values when the measured feature is distant from $\mu_i$. The value of $\sigma_i$ controls how rapidly the value of G decreases as $V(M, P)_i$ moves away from $\mu_i$. FIG. 6A shows a sketch of the shape of the G function.

Given an initial set of training poses, the training process is initialized by providing starting values for each of the parameters. In the preferred embodiment, the values of $u_j$ and $v_{ji}$ are set to small random positive values in the range from 0.0 to 0.2; $\mu_i$ is initialized to be a small amount (1.0) less than the mean of the values of $V(M, P)_i$ for all molecules and poses in the training data set. The value of $\sigma_i$ is initially set to a value of 0.25. The value of n, the number of intermediate sigmoids, is initialized to 1. If inadequate predictions are obtained, n can be increased and the model re-trained until a sufficient value of n is found.

Figure 6B:
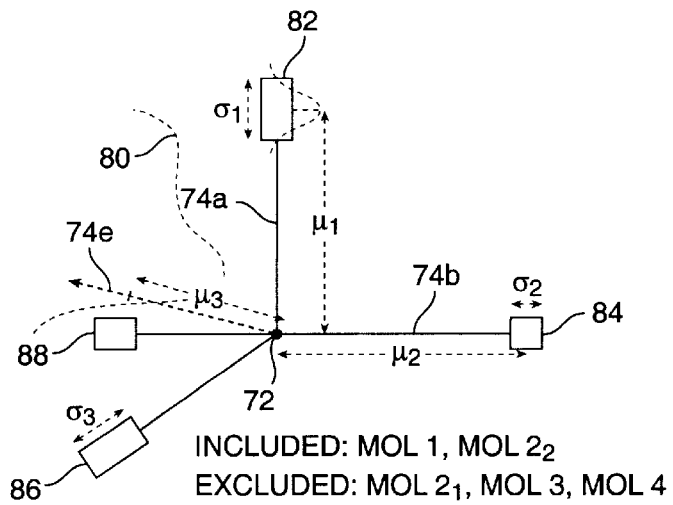
FIG. 6B is a schematic view of a ray-based feature extraction system and tolerance boxes to illustrate the relationship between activity of the molecule and its feature values along the rays of the ray-based system.
Figure 6C:
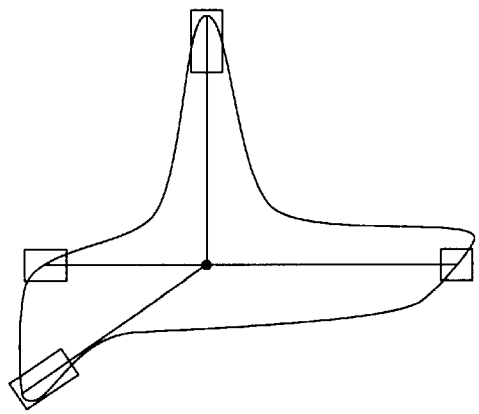
FIG. 6C is a schematic view of the ray-based feature extraction system and tolerance boxes in relation to a pose to illustrate the invention.

FIG. 6B provides a graphical interpretation of the model applied to ray-based features. Each Gaussian G ($V(M,P)_i$, $\mu_i$, $\sigma_i$) can be approximately viewed as a box lying along the ray at a location determined by $\mu_i$. The size (length) of the box is determined by $\sigma_i$. If the values of $V_{ji}$ are positive (for each value of j), then this indicates that in order to exhibit activity, it is desirable that the molecular surface pass through this box. For example, box 82 lies at a position $\mu_1$ along ray 74a. This size of the box is determined by $\rho_i$. As shown in FIG. 6C, molecule 1 falls inside all of the boxes 82, 84, 86 and 88, so (assuming the $V_{ji}$ are all positive), it will have very high predicted activity. If the values of $V_{ji}$ are negative for some ray i, then the box represents a region where the molecular surface should not be located. This is how the model represents excluded regions for the molecular surface.

Because contributions are weighted and summed by the sigmoid functions, a molecule can still have fairly high predicted activity even if its surface does not pass through all of the desirable boxes. Notice that the predicted activity of a molecule will vary as the pose of the molecule varies. For each pose, the molecular surface can intersect the various rays at different points, and hence produce different feature values. The final predicted activity of each molecule is determined by the pose that gives the highest predicted activity among all poses considered for that molecule according to the final learned model.

The discussion in the preceding paragraphs has focused on steric features, but the same mathematical model applied equally well to electrostatic features. The values of $\mu_i$ and $\sigma_i$ for an electrostatic feature i describe an interval ("BOX") of desirable or undesirable values for the feature (depending on the values of $V_{ji}$). In fact, the same mathematical model is applicable to other biological activity types including but not limited to affinity, agonism, potency, receptor selectivity and tissue selectivity.

Neural Network Embodiment

Figure 18:
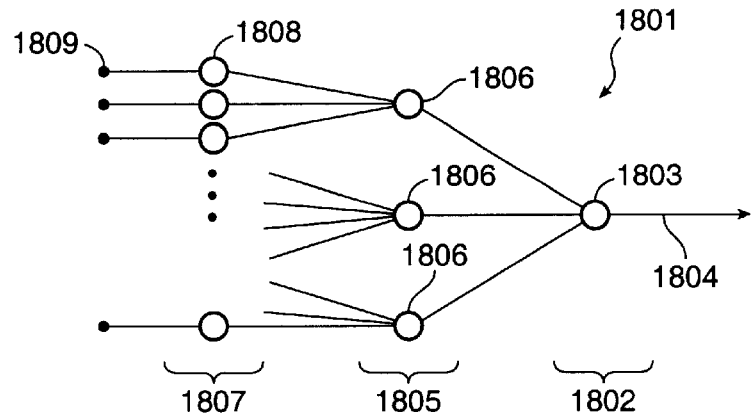
FIG. 18 shows a neural network embodiment of the activity model.

FIG. 18 shows a neural network embodiment of the activity model.

In a preferred embodiment, the neural network 1801 comprises three layers of nodes. An output layer 1802 comprises a single output node 1803, that produces a single output signal 1804 that represents the prediction of activity for the molecule. A second layer 1805 comprises a set of three intermediate nodes 1806, each of which is coupled to the output node 1803. An input layer 1807 comprises a set of input nodes 1808, each is which is coupled to one of the three intermediate nodes 1806.

Each input node 1808 is coupled to a feature value 1809 for the molecule, and each feature value 1809 is one of three types. A first type of feature value 1809 comprises a steric feature value; second type of feature value 1809 comprises a feature value for a polar atom that is a hydrogen acceptor; a third type of feature value 1809 comprises a feature value for a polar atom that is a hydrogen donor.

In a preferred embodiment, each one of the three intermediate nodes 1806 may be trained separately, using only those feature values 1809 coupled to that intermediate node 1806. After each one of the three intermediate nodes 1806 is trained separately, the neural network 1801 is trained for all three intermediate nodes 1806 together using backpropagation or another known method for training neural networks.

Feature Pruning

In a preferred embodiment, selected feature values 1809 are pruned (removed from the set of feature values 1809) after the neural network 1801 is trained.

As described herein, each input node 1808 comprises a Gaussian function 1901 and a sigmoid function 1902. After the neural network 1801 is trained, each input node 1808 is examined for each molecule to determine whether that input node 1808 causes the predicted activation value output by the neural network 1801 is be closer to or farther away from the actual activation value.

If an input node 1808, including both the Gaussian function 1901 and the sigmoid function 1902, makes the predicted activation value less accurate than just the Gaussian function 1901, the sigmoid function 1902 part of the input node 1808 is removed.

If the Gaussian function 1901 part of an input node 1808 makes the predicted activation value less accurate for more than 50% of the molecules in the training set (i.e., the input node 1808 has a prediction capability that is worse than chance), the entire input node 1808 is removed.

The neural network 1801 is then retrained without those input nodes 1808 or parts of input nodes 1808 that have been removed.

Reaularization Procedure

In an alternative embodiment without confidence measures, a regularization process, described herein, may be used in addition to the backpropagation training process. However, the regularization process is not necessary when using confidence measures.

In the regularization procedure, in addition to the back-propagation training process, the z parameter of each Gaussian function may be reduced by a small decrement, such as 0.01, during each training pass. The small decrement should be small enough that it has little effect on the z parameter for any Gaussian feature that is not irrelevant (and therefore is occasionally incremented by the backpropagation training process). The small decrement should also be large enough that its cumulative effect is that the z parameter for any Gaussian feature that is truly irrelevant (and therefore is never incremented by the backpropagation training process) eventually becomes a large negative value.

In the event that the neural network 1801 provides inadequate predictions of molecular activity, additional layers of intermediate nodes 1806 may be inserted between the second layer 1805 and the output layer 1802. These additional layers may comprise a set of intermediate nodes 1806 that are coupled to all the intermediate nodes 1806 of the previous layer (e.g., the second layer 1805) and to the output node 1803.

Neural Network Input Layer

Figure 19:
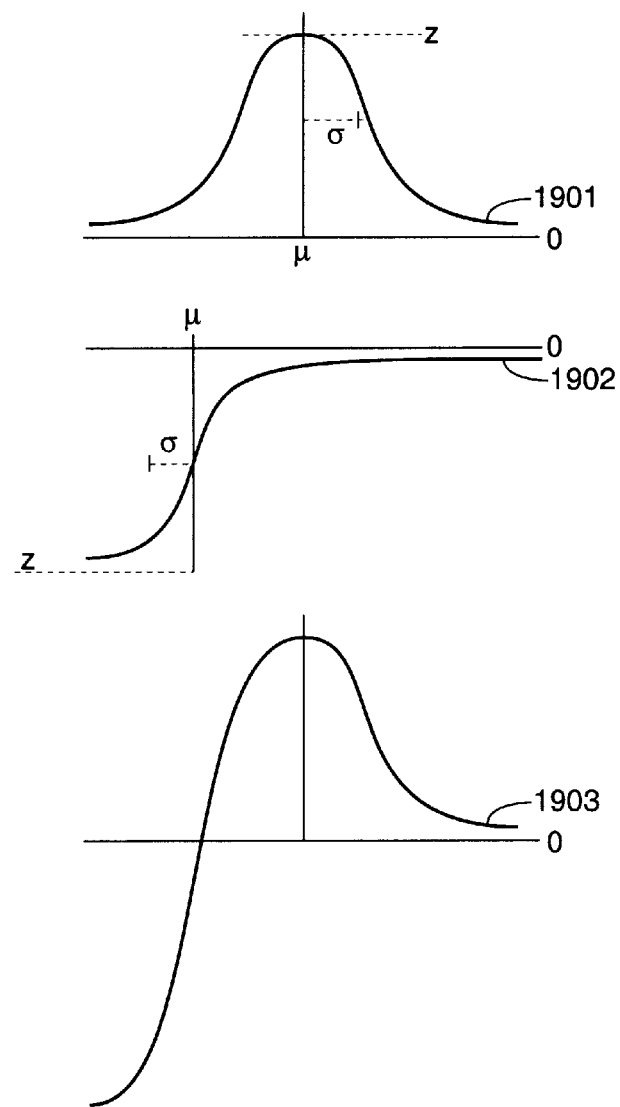
FIG. 19 shows a model of each input node of the neural network.

FIG. 19 shows a model of each input node of the neural network.

In a preferred embodiment, each input node 1807 computes a sum of two functions of its input feature value 1808—(a) a Gaussian function 1901, and (b) a sigmoid function 1902. The Gaussian function 1901 and the sigmoid function 1902 are summed to produce a unified function 1903 of the input feature value 1808.

The unified function 1903 approximates the interaction energy between the molecule and the receptor site, because it has a maximum at the preferred distance, drops off to zero at substantially larger distances, and becomes highly negative at substantially smaller distances. This models the likely behavior of the molecule at the receptor site. The Gaussian function 1901 models the maximum at the preferred distance and the drop-off to zero at substantially larger distances, while the sigmoid function 1902 models the highly negative interaction at substantially smaller distances (where the molecule would likely contend with the receptor site for occupying physical space).

Training the Model

Figure 7:
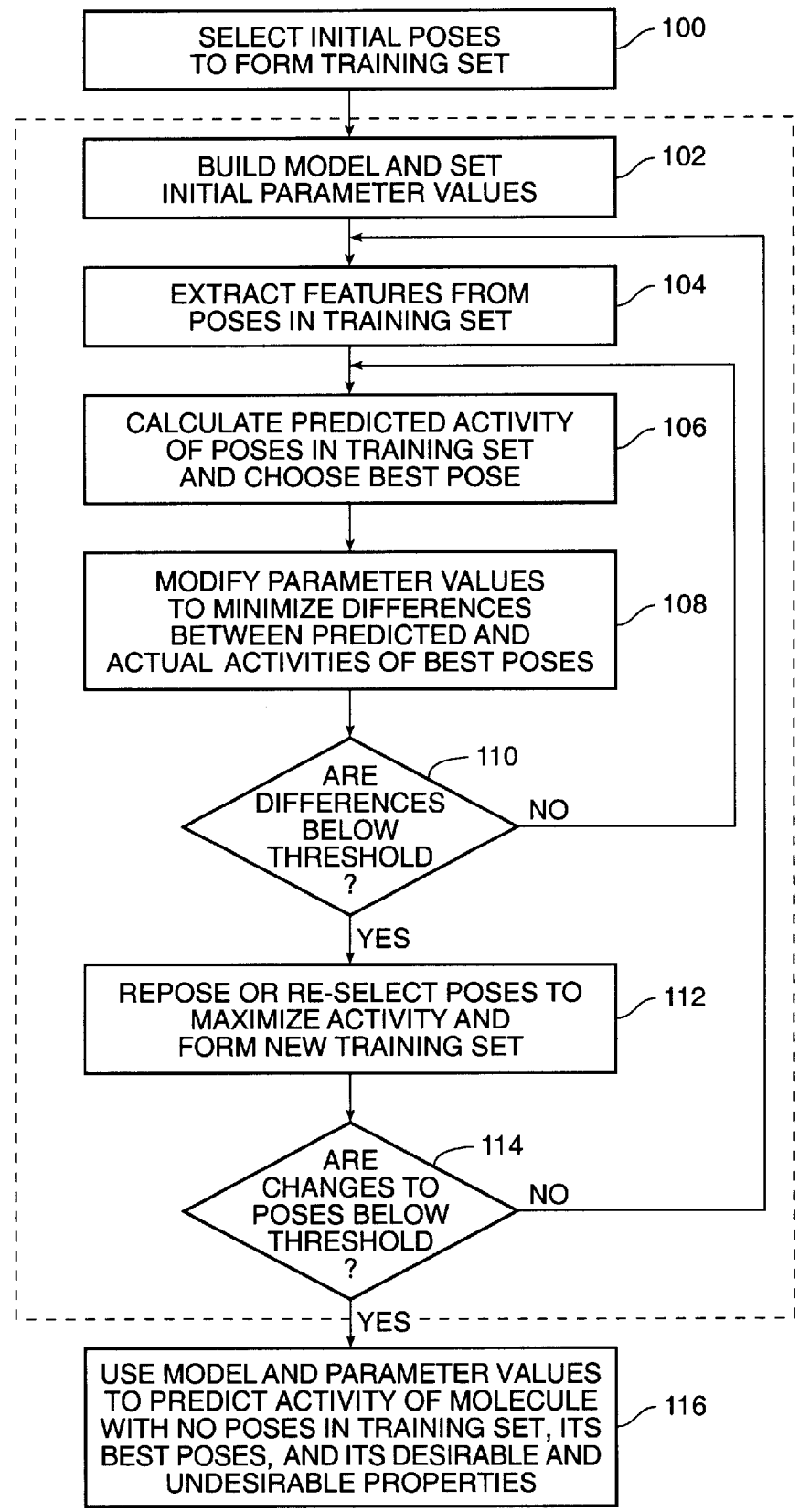
FIG. 7 is a flow chart illustrating iterative model parameter modification and reposing of molecules in order to illustrate the preferred embodiment of the invention.

The training of the model will now be described in reference to FIG. 7. FIG. 7 is a flow chart illustrating in more detail the learning step 24 and prediction step 26 of FIG. 1.

In the preferred embodiment, the sampling points 62 are chosen by reference to an average surface representation obtained by averaging the surface representations of the poses in the training set. Thus, if surface representation 64 is an averaged surface representation of all the poses, then the sampling points 62 are chosen by reference to such surface. The averaging process to obtain the average representation of a set of poses is known to those skilled in the art.

As explained above in reference to FIG. 2, an initial set of poses is selected to form the training set in order to train the model (block 100). Then the initial values for the parameters n, $\mu_i$, $\sigma_i$, $v_{ji}$, and $u_j$ are chosen (block 102). The feature values of the poses in the training set are extracted as described above. However, it will be understood that the training system of the invention is not limited to the point-based or ray-based feature extraction methods above. Then the predicted activity of each of the poses in the training set is calculated using the model and the parameter values set initially by using, for example, the equations above. For each molecule, the pose with the highest predicted activity is chosen as the best pose of the molecule (block 106). Then the parameter values set initially for feature i are modified to minimize the differences between the predicted and actual activities of preferably only the best poses of the molecules.

When receptor sites are present in the vicinity of the molecules used for training, it is known that the presence of such sites would influence the orientation and conformations of molecules present so that in actual fact, the molecules would repose under such influence to attempt to conform to the pose with the highest activity. Therefore, the above-described step in block 108 of training the model by reference to only the best poses of molecules resembles the physical process. It is of course possible to modify the parameter values in reference to poses in addition to or other than the best poses; all such variations are within the scope of the invention.

If $p_j$ is the predicted activity of a particular pose j and $a_j$ its actual activity, then an error function for the training set of poses can be formed by the following equation:

$$Error\ Function = \sum_{j=1}^{m}(p_j - a_j)^2$$

where m is the total number of poses (preferably only the best poses) in the set in reference to which the parameter values are to be modified. A wide variety of computational methods may be applied to minimize the error function with respect to the parameters of the model (e.g., $u_j$, $v_{ji}$, $\mu_i$, $\sigma_i$, n). Such methods are known to those skilled in the art and will not be described here. In the preferred embodiment, the gradient of the error function with respect to these parameters (except for n) is computed, and gradient descent methods are applied. Other methods such as conjugate gradient, Newton methods, simulated annealing, and genetic algorithms may also be used and are within the scope of the invention.

After the differences between predicted and actual activities of poses (e.g., best poses) have been minimized, such as by minimizing the above error function, such differences are compared to preset thresholds (diamond 110). If the differences are below the preset threshold or thresholds, one concludes that the process has converged and proceeds to the step in block 112. If not, then one returns to block 106 to calculate the predicted activities of poses in the training set by reference to the modified parameter values and again choose the best pose for each molecule having the highest predicted activity. The parameter values are again modified to minimize differences between predicted and actual activities of best poses. This loop is repeated until the differences are found to be below preset threshold or thresholds and the same best poses are chosen every time.

Figure 8A:
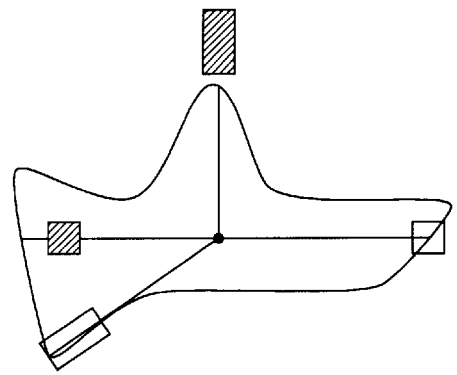
FIGS. 8A–8C and 9A–C are two sets of figures each set showing a molecule undergoing re-orientation and re-conformation to illustrate the preferred embodiment of the invention.
Figure 8B:
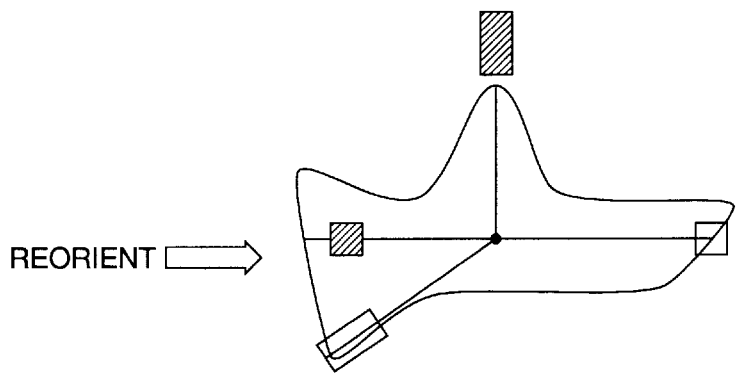
Figure 8C:
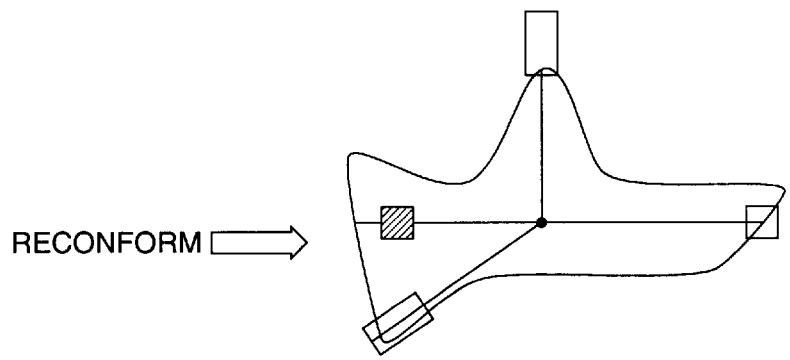
Figure 9A:
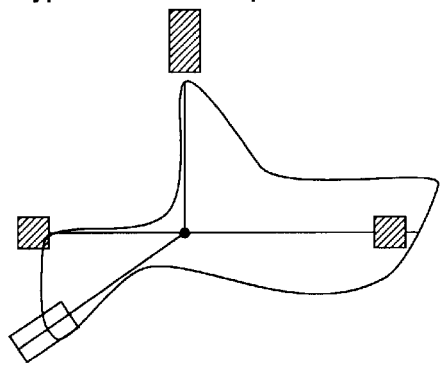
Figure 9B:
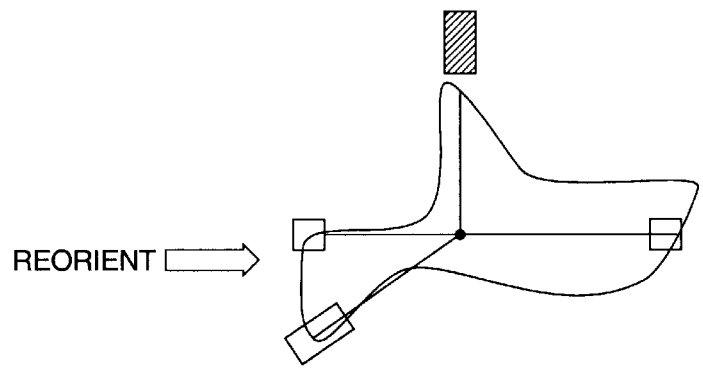
Figure 9C:
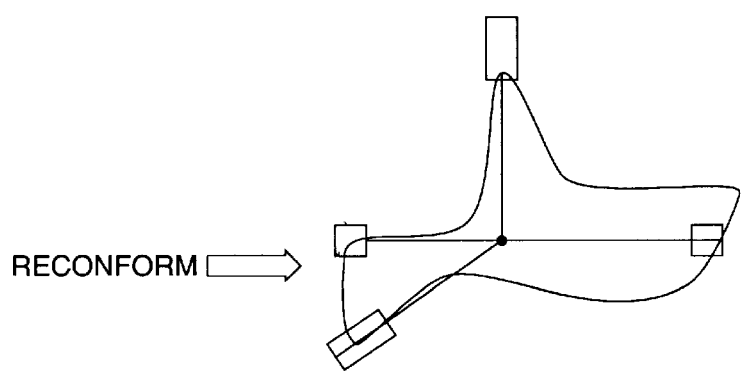

Then the molecules are reposed to maximize their activities and from the possible poses after the reposing, poses are chosen to form a new training set (block 112), a process such as that illustrated in FIG. 2 above. Instead of reposing the molecules, it is possible to simply re-select from the initial set of poses to form the training set of poses, as illustrated in FIG. 2. However, it is believed to be preferable to repose the molecules in order to form a new training set. The new training set is compared to the prior training set to see whether the changes to the poses are below certain set threshold or thresholds (diamond 114). If the changes are found to be below the threshold(s), then the process of training the model is completed and one proceeds to the prediction step in block 116. If the changes to the poses are not below the threshold or thresholds, (diamond 114), then one returns to block 104. Since the orientation and conformation of the poses may have changed, these new poses will have different feature values from those in the original training set. Therefore, the feature extraction step needs to be repeated. The process of reposing is illustrated in FIGS. 8A–8C and 9A–9C by reference to a ray-based system. As shown in FIGS. 8A, 8B, molecule 3 is reposed by first re-orienting the molecule with respect to the sampling points (or to the rays in the ray-based system). When the parameter values of the model are modified, the positions of the boxes in FIG. 8 have been modified so that they are not the same as the positions of the boxes in the prior application of the model to the molecule. Therefore, molecule 3 has been re-oriented to best fit its surface portions within the tolerance boxes with positive weighting factors and to avoid boxes with negative weighting factors as shown in FIG. 8B. Then the internal torsion angles of the rotatable bonds are altered to re-conform the molecule to again best fit the surface portions of the molecule within the modified boxes as shown in FIG. 8C. Molecule 3 is known to have low activity. As illustrated in FIG. 8C, the molecule cannot be maneuvered to fit into one of the tolerance boxes. This may cause the calculated predicted activity of molecule 3 to be low as well so that the model is confirmed. Molecule 4 is re-oriented and re-conformed in a manner similar to that for molecule 3. As shown in FIG. 9C, molecule 4 can be reposed so that its surface portions fit within all the tolerance boxes of the model. This may cause molecule 4 to have a high predicted activity, contrary to the known low activity of the molecule. If this happens, this may cause the error function to exceed the preset threshold(s) so that the parameter values would have to be modified again as described above for the inner loop in blocks 106, 108 and diamond 110.

The above-described process makes good use of the salient feature of poses of inactive as well as active molecules. The above-described reposing process with aligned and conformed poses of active molecules to maximize the activities and to repose the inactive molecules to be in the best position to refute the model. Thus, in order for the model to pass the above-described testing process, it will predict the inactivity of poses of inactive molecules even though these have been realigned and reconfirmed to be in the best position to "fool" the model, while at the same time confirming the activity of the active molecules.

In the preferred embodiment, gradient search methods are also used for reposing the training molecules to maximize their predicted activities as functions of the orientation and conformational parameters.

For both the point-based and ray-based feature extraction methods used in conjunction with either the van der Waals or Connolly surfaces, the extracted features are differentiable functions of the orientation and conformational parameters. Furthermore, the model (as represented by the equations above) is a differentiable function of the values of the extracted features. Hence, by applying the chain rule, it is possible to compute the gradient of the predicted activity with respect to the orientation and conformational parameters and apply gradient-based search to find poses that maximize predicted activity. However, other kinds of models and other methods of feature extraction may not satisfy this property, in which case other computational methods (e.g., simulated annealing, linear programming) could be applied to find poses that maximize predicted activity. It is understood that the scope of the invention includes all methods for finding such poses.

Instead of reposing the molecules, it is possible to simply re-select the best poses from the original set of poses formed prior to the selection step in block 100. It is found, however, that reposing the molecules rather than re-selecting from existing poses greatly reduces the error of prediction as indicated in Table 1 below in regard to a musk model.

The trained model and the ultimate parameter values may then be used to predict the activity of a new molecule with unknown activity (block 116). Thus, again, feature values are extracted from the poses of the molecule and the predicted activities of the poses are calculated to find the best pose with the highest activity. Thus, the model not only enables the user to predict the activity of the molecule not in the training set but also predict its best poses. Its feature values in comparison with the parameter values would indicate which surface portions have the desirable properties in regard to a chemical function and which surface portions have undesirable properties in regard to such function. This is illustrated in more detail in FIGS. 12A–12F and the accompanying description below. In fact, the model may be used to search a database of molecules with unknown activity and predict the activities of their poses. Poses of these molecules may be modified to alter their predicted activities.

In FIG. 7 above, the model parameter values are optimized in an inner loop before the molecules are reposed or poses reselected in an outer loop. Such embodiment is efficient because reposing molecules requires large numbers of calculations. It will be understood, however, that the optimization can be performed in ways different from that described above and are within the scope of the invention. For example, it is possible to maximize the activity by reposing in an inner loop before the model parameter values are optimized to minimize the differences between predicted and actual activities of best poses in an outer loop. The two optimization processes may also be intertwined.

In the above-described point based feature extraction using a van der Waals surface representation of atoms, it will be simpler not to have to first calculate the surface representations of the entire molecule but simply to determine the closest distance between a particular sampling point and find the atom whose van der Waals surface will be at the closest distance to such sampling point. In order to determine the nearest atomic surface to a sampling point, one way requires computing the distance between the sampling point and the van der Waals sphere computed for each atom in the molecule separately. For each atom in the molecule, the distance d between a sampling point p with coordinates (px, py, pz) and the van der Waals sphere of radius r for an atom with a center at c with coordinates (cx, cy, cz) is:

$$d = \operatorname{sqrt}((px-cx)^2 + (py-cy)^2 + (pz-cz)^2) - r$$

This requires computing a square root, for each possible atom, which is very expensive. Another aspect of the invention provides a much more efficient way to compute this distance d, based on the observation that it is cheaper to compute the square of the distance than to compute the distance itself. The nearest-atom computation operates in two passes on each feature. In the first pass, we find the minimum distance squared to atomic centers. The atom with the minimum distance to atomic center is not necessarily the atom with the minimum distance to the van der Waals surface, however. Therefore, in the second pass, the distance to the van der Waals surface distance is determined only for atoms that are "close" to the minimum distance squared. It is noted here that the distance to the van der Waals surface distance cannot be computed in distance squared space, because of the subtraction of the van der Waals radius. In the second pass, "close" is computed in terms of the difference between the radius of the atom with the minimum distance squared to center and the maximum possible atomic radius.

Figure 10:
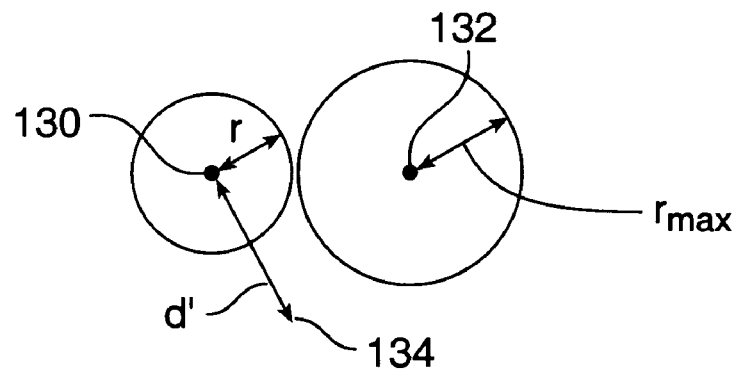
FIG. 10 is a schematic view illustrating a method for finding the minimum distance between the sampling point and the van der Waals surfaces of atoms of a molecule to illustrate the invention.

Specifically, in reference to FIG. 10, suppose the atom with the minimum distance squared to its center 130 has distance d' to the sampling point 134 and radius r. Suppose the atom in the molecule centered at 132 with the maximum radius has radius $r_{max}$. Then an atom center (e.g. 132) of another atom could in principle be up to $d' + r_{max} - r$ away and have the same distance to the van der Waals shell viewed from point 134 as the atom centered at 130. So we want to look at all atoms close to center 130 but whose distance squared to atomic center is within $(d'+r_{max}-r)^2$ away. Thus, in the second pass, we look at atoms in the vicinity of 130 with van der Waals radii between r and $r_{max}$ using a square root calculation.

Example

The relationship between the model parameter values and the poses of the molecules may be displayed visually using computer graphics to aid biochemical design as in the musk odor prediction problem described below. Thus, the parameter values $\mu_i$, $\sigma_i$ and weighting factor $v_{ji}$ discussed above may be displayed on a screen of a monitor as well as a surface of a molecule. The model parameter values may be illustrated by octagonal patches near the surface of the molecule where each feature was measured. Each patch is colored according to whether the measurement found the surface to be too close, too far, or about right. These three values are computed by thresholding the Gaussian corresponding to each feature. clearly, a Gaussian with a wide a will allow a broader range of distance measurements to count as "about right."

When the surface is too far from the measurement point, there may be room to modify the molecule to add additional bulk to the molecule. When the surface is too close to the measurement point, there may be need to modify the molecule to trim bulk from the molecule.

Thus, the pattern of colored patches may guide the medicinal chemist in choosing the parts of the molecule which should be made larger or smaller to improve the activity of the molecule.

The problem of musk odor prediction has been the focus of many modeling efforts. Musk odor is a specific and clearly identifiable sensation, although the mechanisms underlying it are poorly understood. These molecules typically have a single hydrogen-bond acceptor on a roughly ellipsoidal hydrocarbon. Musk odor is determined almost entirely by steric effects. A single methyl group change can account for a significant change in musk odor.

To test the invention's ability to predict subtle steric interactions, we studied a set of 102 diverse structures in several chemical classes collected from published studies. only those compounds for which published assay values agreed were used. The data set contained 39 aromatic, oxygen-containing molecules with musk odor and 63 homologs that lacked musk odor. Each molecule was conformationally searched using a Monte Carlo procedure. Some molecules possessed flexible sidechains and exhibited a sizeable number of conformations (ranging from 2 to over 250), many of which significantly changed the overall shape of the molecule. Because all molecules were assayed as racemic mixtures, all stereoisomers of each molecule were likewise searched and included in the data set. The final dataset contained 6,953 conformathons of the 102 molecules.

TABLE 1

Predictive accuracy of musk model in a 20-fold cross-validation hold-out test (standard error is in brackets).

|  | True Pos. | False Neg. | True Neg. | False Pos. | % Correct |
| --- | --- | --- | --- | --- | --- |
| Adaptive alignment | 36 | 3 | 57 | 6 | 91[2.8] |
| Fixed alignment | 36 | 3 | 47 | 16 | 81[3.9] |

Figure 11:
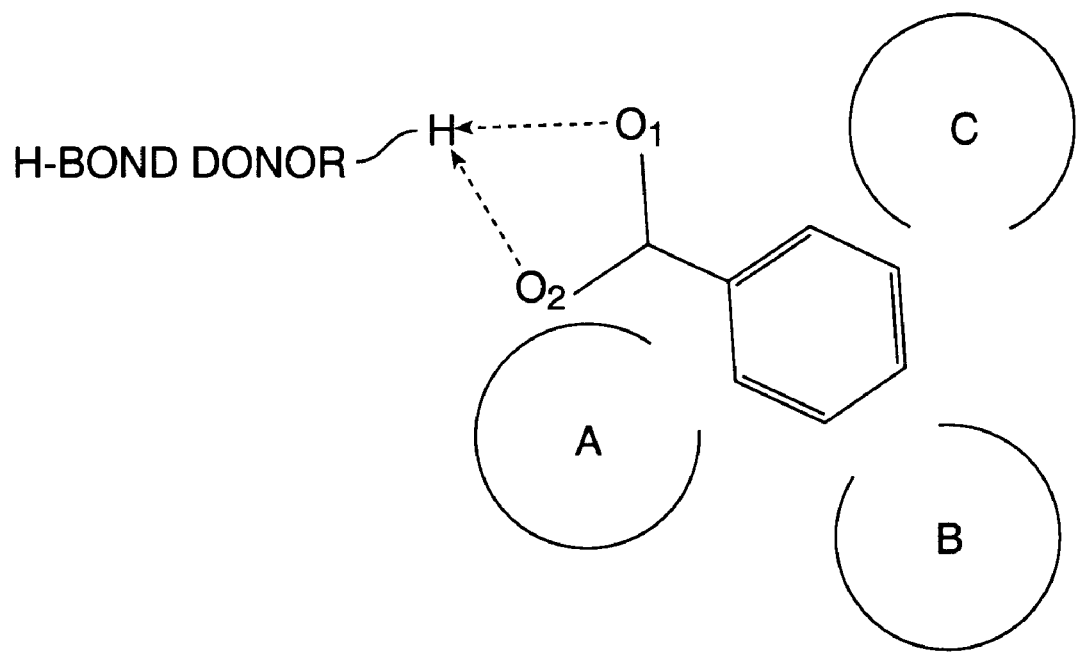
FIG. 11 is a crude diagram of learned requirements for musk odor activity to illustrate an example applying the invention of this application.

We performed a 20-fold cross-validation test of predictive performance. The molecules in the data set were partitioned into twenty random subsets. Twenty models were trained, with one of these subsets excluded from the training data during each execution. The model constructed in each execution was then tested to see how well it could predict the withheld molecules, and the results were totalled. Overall predictive performance using is 91% (see Table 1). In Table 1, "True Pos." means that a molecule which is active is confirmed to be active, "False Neg." means that an active molecule is erroneously predicted to be inactive, "True Neg." means that an inactive molecule is predicted to be inactive, and "False Pos." means that inactive molecules are erroneously predicted to be active. A model constructed using fixed molecular alignments results in predictive performance of 81%—the model-directed realignment (i.e., reposing) aspect of the invention substantially improves performance. The primary requirements of musk activity discovered by applying the invention are crudely illustrated in FIG. 11 (the actual learned models are sensitive to approximately fifty specific surface regions). Molecules must have a hydrogen bond acceptor at the appropriate geometry (positions 1 or 2), and the right amount of hydrophobic bulk at positions A, B and C. This model is consistent with other models of musk odor activity, but it was learned exclusively from a general surface-based representation of shape.

Predictive models must be able to extrapolate beyond the structural classes analyzed during model generation to be useful for molecular design. Random hold-out tests, such as cross-validation, do not test this ability because they mix all structural classes in both the training and test data. To test extrapolation ability, we conducted a series of class-holdout experiments in which all molecules of a given structural class were withheld during training and then evaluated during testing. This simulates the situation in which chemists wish to apply a learned model to guide the synthesis of a new class of compounds. Table 2 shows four classes, the largest of which is class 2. Class 1 has a substantially different arrangement of hydrophobic bulk. Classes 2 and 4 have molecules with different hydrogen-bonding geometries. Each class represents a structural type that a chemist might choose as a synthetic target.

Cross-class predictive performance ranges from 71% to 100% and in all cases benefit substantially by using adaptive alignment (i.e., iterative reposing and model parameter value modification)—the error-rate drops by more than half. A more useful criterion in assessing performance than percent correctly predicted above or below a fixed threshold is the quality of the ranking of the molecules as measured by the number of molecules that are misranked. The neural-network produces a value on the interval [0,1], and test molecules are ranked by this score. A ranked list is perfect if all active molecules are ranked higher than all inactive molecules. The number of misranked molecules is the minimum number of molecules that need to be eliminated from the ranked list to produce a list with a perfect ranking. This is different from other rank scores because the musk data contains only binary assay values but the invention makes real-valued predictions. By this measure, with adaptive alignment, predictive performance is very high, ranging from 86% to 100%. Performance on class 4 is the poorest and seems to be related to the non-planar geometry of the ether component of these molecules.

TABLE 2

Predictive accuracy of musk model across structural classes.
Numbers in brackets are standard error.
The counts reported in rows 2–4 are for adaptive alignment.

| Structural Class: | (1)4-substituted dihydro-indanes | (2)1-indanones | (3)6-substituted(4) tetrahydro-napthalenes | benzo-pyrans |
|---|---|---|---|---|
| Number of molecules | 13 | 21 | 27 | 14 |
| True positives | 7 | 6 | 9 | 4 |
| False negatives | 0 | 0 | 4 | 3 |
| True negatives | 6 | 13 | 13 | 5 |
| False positives | 0 | 2 | 0 | 1 |
| Percent correct (adaptive alignment) | 100[0.0] | 90[6.5] | 85[6.8] | 71[12.1] |
| Percent correct (fixed alignment) | 85[9.9] | 76[9.3] | 74[8.4] | 57[13.2] |
| Number misranked | 0 | 1 | 1 | 2 |
| Percent correct (by ranking) | 100[0.0] | 95[4.8] | 96[3.8] | 86[9.3] |

Previous studies of musk odor on similar molecules using atom-based approaches have produced similar levels of predictive accuracy in cross-validated predictive tests, ranging from 90% (std. err. 6.7) to 93% (std. err. 6.4). However, none of these studies has reported predictive results across chemical classes or has employed molecular properties that could easily be interpreted to guide design of new compounds.

To illustrate the system's ability to provide detailed guidance in molecular design, additional models were trained while withholding specific pairs, triplets, and quadruplets of molecules that differed by single methyl group additions and deletions. FIGS. 12A–12F depicts six molecules, each processed by a model. The molecules are displayed in their most active predicted poses (chosen by the model) with a Connolly surface. M. J. Connolly, *J. Appl. Cryst.*, 16, 548 (1983). The patches on each surface correspond to the set of features selected by the model. The surface has an acceptable steric interaction if it has a gray patch at that location. White patches indicate areas that should be increased in size, and black patches indicate areas whose size should be decreased.

Figure 12A:
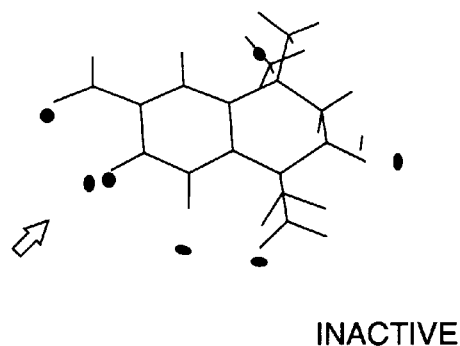
FIGS. 12A–12F are graphical illustrations of six different molecules showing the relations between their structures and activities to illustrate the invention.
Figure 12B:
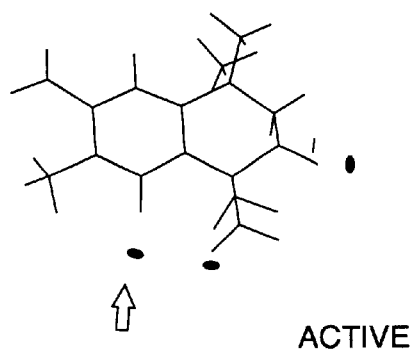
Figure 12C:
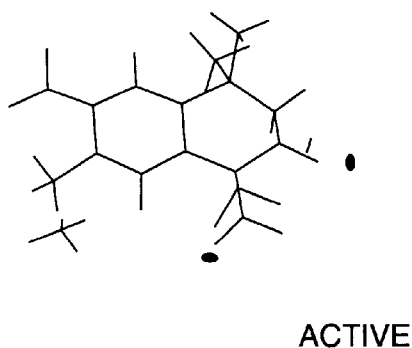
Figure 12D:
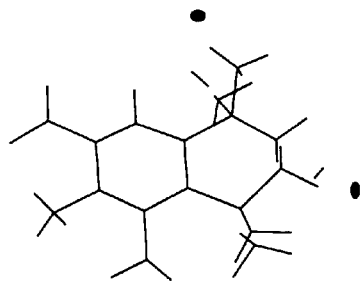

The method's ability to provide detailed guidance in molecular design is demonstrated in FIGS. 12A–12F. Only black, gray and white patches are shown in these figures since color patches cannot be reproduced in patent drawings. FIGS. 12A–12D display four molecules in their predicted poses as chosen by a model trained on the remaining ninety-eight molecules. Each molecule is displayed as a Connolly surface. The relative musk odor strength of these four hold-out molecules is known. The patches on each surface correspond to the features selected by the model during training. The surface has a good steric interaction if it has a gray patch at that location. White patches indicate areas that should be increased in size, and black patches indicate areas whose size should be decreased. FIG. 12A displays a correctly predicted inactive molecule, and the white patches suggest that activity could be increased by adding bulk near the arrow (corresponding to area A in FIG. 11). FIG. 12B shows the molecule resulting from the addition of a methyl group at this point, correctly predicted to have musk odor. From this molecule, which has only moderate musk odor intensity, the indicated region (corresponding to area B of FIG. 11) is predicted to benefit from additional bulk. Either adding a methyl group to the aromatic ring, shown in FIG. 12C, or changing the methyl group added to FIG. 12A to an ethyl, achieves this result. Both the molecules in FIGS. 12C, 12D have greater musk odor than molecule in FIG. 12B, as predicted.

Figure 12E:
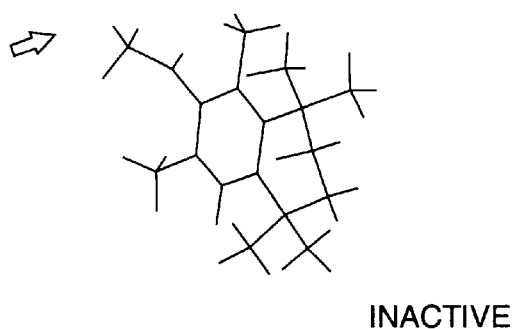
Figure 12F:
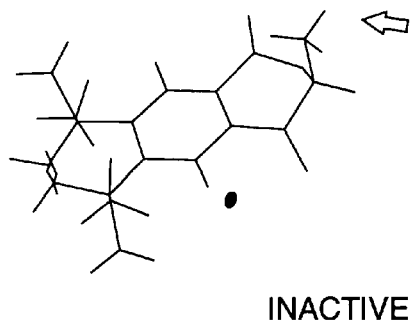

FIGS. 12E, 12F show the application of another model, constructed by withholding the pair of molecules shown. FIG. 12A, the black patches suggest an unfavorable interaction (indicated by the arrow). This can be directly remedied by removal of the corresponding methyl group. The result is a correctly predicted molecule with strong musk odor, shown in FIG. 12B. Another approach is to remove the methyl substituent on the aromatic ring that is responsible for the ketone's unfavorable orientation. This results in a molecule of medium musk strength (not shown). Several other examples of guided design on molecules from different structural classes in this data set were observed.

What follows is a detailed description of predictive model generation from a set of molecules and assay values. We first discussed the surface representation, then the neural-network learning algorithm, then the adaptive alignment procedure. Consider a molecule in a particular conformation at a particular location and orientation in space. This situation is defined by the internal torsion angles of the rotatable bonds, and the three rigid rotations and translations. This mathematically defines the pose of the molecule. From each pose p of a molecule m, we generate a high-dimensional vector of features $V(m,p)$ for purposes of activity prediction. Each element of the feature vector characterizes a portion of the smoothed van der Wall's surface of the molecule.

Our goal is to predict the activity of a molecule as a function of the feature vector. However, because there are infinitely many poses of molecule, there are infinitely many feature vectors. Let $A(V(m,p))$ denote the predicted activity of molecule m in pose p. The predicted activity for m is defined to be the maximum of these predictions over all possible (low energy) poses: $\text{Max}_{low\ energy\ p} A(V(mtp))$. In chemical terms, this is analogous to permitting the molecule to rotate, translate and alter its conformation to achieve the best possible fit to the binding site.

To achieve this maximization, we conduct a conformational search for each molecule to identify its low-energy conformations. Each of these conformers is placed in a starting pose, and the learning algorithm is applied to construct a model $A(V(m,p))$. For the application reported here, initial poses were chosen such that their aromatic rings were tightly aligned and their oxygens were properly positioned to form a hydrogen bond with an assumed H-bond donor atom (34, 35). This produced an acceptable coarse alignment of the molecules. The model computes a weighted sum of non-linear functions, which can be cascaded, whose parameters can be estimated to achieve a mapping from input molecular features to an output activity value. The activity of musks was encoded as 0.982 and the activity of non-musks was encoded as 0.018. A molecule was predicted to be a musk if the model computed its activity to be greater than 0.5. Such models are called neural networks because of the analogy to biological neural networks where the "neurons" compute non-linear functions based on weighted and summed input ("synaptic connections") from other neurons.

Our model is of the form:

$$A(m_i) = \underset{p \in P}{\text{Max}} \text{Sigmoid}\left[\sum_{j=1}^{m} F\left[\vec{v}_j, \sum_{k=1}^{n} G(\vec{w}_k, V(m_i, P))\right]\right]$$

where F, G are non-linear functions. The vectors $v_j$, j=0... m and $w_k$, k=1... n are vectors of adjustable weights. The set P is the set of poses generated thus far. The model is trained by an iterative weight adjustment procedure that seeks to minimize error using gradient-based search, called error back-propagation. D. E. Rumelhart, G. E. Hinton, R. J. Williams, in "Parallel Distributed Processing: Explorations in the Microstructure of Cognition," D. E. Rumelhart, J. L. McClelland, and the PDP Research Group, Eds. (MIT Press/ Bradford, Cambridge, Mass. 1986), Vol. 1: Foundations. For each molecule, only the pose giving the highest predicted activity (using the current model) is used to update the weight vectors.

In each iteration, after the neural network model has been trained, it is applied to each molecule $m_i$ to find the pose $p_i$ that maximizes the predicted activity of $m_i$ by performing rigid rotations and translations. This is accomplished by computing the gradient of the predicted activity with respect to the pose and employing gradient search methods. The poses computed in this fashion for the active molecules are precisely those poses that serve to confirm the model—they cause the active molecules to align more tightly with each other along those portions of the molecular surface that are important for activity prediction. The poses computed for inactive molecules are precisely those poses that best refute the model. Hence, we see that this algorithm applies a simple form of the scientific method of conjecture and refutation until a model is found that cannot be refuted. To attain convergence, at most five iterations of model-building and pose generation were required. The advantage of this approach is that only a small fraction of the infinite space of possible poses needs to be explicitly considered, and yet the resulting model is robust with respect to a much wider range of poses of the molecules. It also makes good use of negative data.

This adaptive approach to posing molecules is a major departure from previous methods. Any method that attempts to measure subtle shape differences among molecules must measure molecular properties (e.g., interatomic distances, occupancy of binding sites) that vary with pose. Previous methods assume that the correct poses of molecules can be selected before a predictive model is constructed. Models constructed from standard fixed poses may not give accurate predictions for new molecules. New molecules must be placed in the appropriate pose based on intuition or ad hoc procedures that may behave poorly, especially with molecules from novel structural classes. Our approach, in contrast, uses the constructed model to guide the generation of the correct poses, so that molecules are aligned along those surface regions that are most predictive of activity differences.

We have demonstrated a new method for activity prediction and molecular design using a surface-based representation of molecular shape that exhibits high predictivity and extrapolates well across structural classes. Automatic selection of conformations and adaptive alignment of molecules was shown to substantially improve predictive performance. Three-dimensional visualization of models guided structural changes of molecules that enhanced biological activity. The surface-based molecular representation yielded excellent cross-class predictive performance, a capability which is critical for advancing drug design into new structural classes. The model was able to resolve the effects of very subtle surface changes.

Where the known activities of the molecules are expressed in quantitative terms, the above-described model can be readily applied using the quantitative known activities. Where the activities are non-numerical, such as in the musk study above, musk strength prediction is somewhat complicated. The reported strengths are discrete non-numerical values; for example, "extremely strong" and "fairly weak." There are about ten such values. How do we map "medium strength" to a number?

We could use an arbitrary mapping, like "odorless" is 0.1 and "very weak" is 0.2 and "weak" is 0.3, and so on. But there is a potential problem. There is, in some sense, a "right" answer. Assuming no hidden units, the output is essentially a linear sum of the feature inputs. There may not be any linear weighting that gets very close to an arbitrary assignment of numbers to strengths. The curve is kinked. The system will devote a lot of effort to trying to unkink it.

As an alternative, we let the system figure out what the true assignment of discrete categories to numerical values is. The target value for each category is initialized arbitrarily, with correct ordering, as above. But then it can float. We backpropagate the error term for each category into the target value for the category. So, during training, we periodically look at the output of the model for all the "medium" musks and take the average, say 0.56. Then we adjust the target for "medium" molecules from its current value (say 0.52) in the direction of the average. This reduces the error for all the medium molecules (since the error is computed as the difference between the actual and target values).

The learning rate parameter for this backpropagation has to be set low, so that the system does not thrash trying to fix gross errors in the model by adjusting the target values.

It may be necessary to permanently wire the extreme values ("odorless" and "extremely strong") to 0.1 and 0.9 to avoid having the system reduce error by collapsing the scale.

It is possible that for various reasons (e.g., bad assays), even with a low learning rate the targets could cross (so that, e.g., "medium" got to be higher than "fairly strong"). We could fix this by adding a $1/r^2$ "repulsive force" to the targets, so that in the target update phase as two targets got close to each other, they would be held apart. (This would also have the side effect of preventing scale collapse.)

This level of indirection between the reported assay values and the system's target values can also be used to make assay values reported from different sources commensurable. This applies to both numerical and non-numerical assays. Commonly, one paper in the literature will report assay values for one set of molecules and another paper will report assay values for another set. Particularly, if the sets are disjoint, these values may not be commensurable, since the assays typically were performed under somewhat different conditions. Now, we have the correct ordering for the assay values on a per-source basis (and also the within-source relative magnitudes, in the case of numerical data). The target-score adjustment code will respect that, but between papers, one can let the system do as it pleases and decide, for example, that one paper is 0.05 is equivalent to other's 2.7.

Confidence Estimator

In a preferred embodiment, an confidence estimate is determined simultaneously with a prediction of molecular activity. A concept underlying the confidence estimate is that the model can only predict well for features that it has seen a reasonable number of times in training molecules with that feature. Accordingly, a confidence estimate is determined for each prediction for each molecule in response to the feature values of that molecule.

For each feature value of the molecule, a nearest neighbor value is determined in response to the closeness of the feature value to the difference from closest value for that feature in the training set. In a preferred embodiment, the nearest neighbor value is an absolute value of that difference.

For each feature value of the molecule, an outlier value is determined in response to the difference of the feature value from the mean value for that feature in the training set. In a preferred embodiment, the outlier value is an absolute value of that difference.

For each feature value of the molecule, a weight is assigned to the feature value in response to its importance in predicting activity of molecules in the training set. In a preferred embodiment, the weight is inversely proportional to the z score for the Gaussian function 1901 associated with that feature value.

A confidence estimate for a molecule is formed in response to the nearest neighbor value, the outlier value, and the weight for each feature value for that molecule. In a preferred embodiment, the nearest neighbor value and outlier value are summed, and the weighted average of such sums for all feature values is determined, where each sum for a feature value is weighted by the weight assigned to that feature value.

Generality of the Invention

Two aspects of the invention descried above, the method of iterative reposing objects to produce better models and the method of training a model when each object has multiple representations, are applicable not only to biological activity modeling but also to many other problems including handwriting recognition. We illustrate this with the task of handwritten character recognition.

Figure 13:
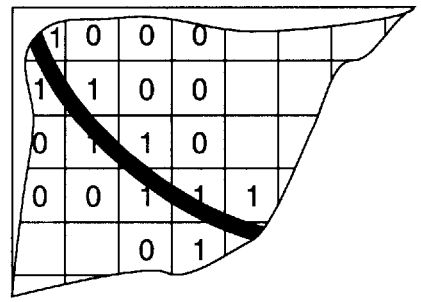
FIG. 13 is a schematic view of a portion of a 16×16 grid to illustrate a machine-learning method for predicting characteristics of objects to illustrate another aspect of the invention.

Computer methods for automatically recognizing handwritten characters would be extremely useful in several fields including the reading of zip codes on envelopes, dollar amounts on personal checks, and handwritten characters on pen-based computers. An accepted way of representing handwritten letters for automated recognition is to take a digital picture of each letter. The picture represented in the computer by, for example, a 16×16 grid of binary values (a part of which is shown in FIG. 13). These two hundred fiftysix values become the features that can be input into a general purpose classification algorithm, such as a neural network. As with the molecules discussed above, each character can be defined to have a "pose." For example, a character can rotate or translate in two dimensions as well as be scaled larger or smaller. The pose of a character can be defined by a set of parameters (e.g., two rotational parameters, two translational parameters, and one scale parameter).

Figure 14:
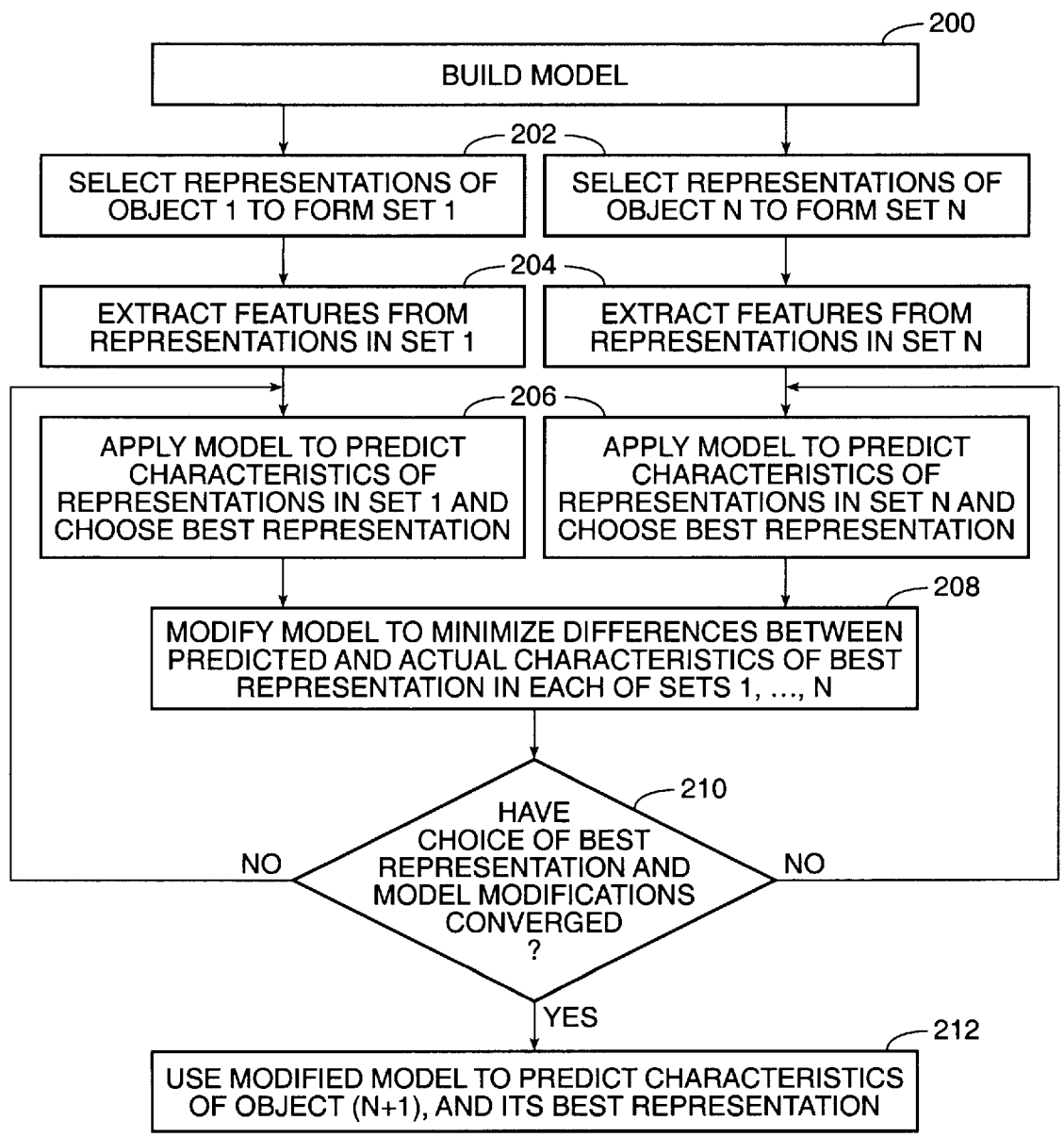
FIG. 14 is a flow chart to illustrate the aspect of the invention of FIG. 13.

Let us first consider how the general machine learning method of learning from multiple representations could be applied to this task. Suppose we wish to automatically recognize instances of the letter 'A.' A training set could be constructed consisting of a large number of digitized handwritten 'A's as well as a large number of other characters and symbols from which the 'A's need to be discriminated. Then the general procedure shown in FIG. 14 could be applied.

First (block 200), a neural network model for 'A' could be initialized. Each of the N different characters and symbols forms a training object. Then (block 202), for each object in the training set, a set of poses could be generated by computing several different combinations of rotations, translations, and scalings of each character (set 1, . . . , set N). Features (e.g. 256 values in a 16 by 16 grid) would be extracted (block 204) and then the neural network model would be applied to predict whether each of the representative poses was an instance of the letter 'A' (block 206). Based on the predicted scores, one or more best representative poses of each object in the training set would be selected, and the neural network model would be trained to predict correctly whether each pose was an instance of the letter 'A.' If the model and the choices of best representations do not change substantially from previous iterations (block 21), then the process terminates. otherwise, the current model is applied to all of the poses of each object in the training set (block 206) to again select one or more best representations for each object.

Once the model and the choice of representations converges, the learned model can be applied to predict whether or not new objects are instances of the letter 'A' (block 212). The same procedure could be applied to construct recognizers for each of the other letters of the alphabet, the digits, punctuation symbols, and so on.

Now that we have described how the general machine learning method could be applied to character recognition, let us consider how the method of dynamic reposing (not shown in FIG. 14) could also be applied to this problem. The method is exactly analogous to FIG. 7. As above, we begin with a training set consisting of a large number of digitized handwritten 'A's as well as a large number of other characters and symbols from which the 'A's need to be discriminated. Rather than generating many different poses of each character, we would compute initial poses by rotating, translating, and scaling the characters in the training set so that they all had approximately the same orientation and size. This corresponds to block 100 of FIG. 7. Then a neural network training procedure is carried out (blocks 108, 110). After training the model, the key component of this aspect of the invention would be applied. The current trained model would be used to guide the reposing of each of the training set characters (block 112) in an attempt to maximize the predicted output of the neural network (i.e., to maximize the likelihood that the network would predict that each character was an 'A'). The resulting poses would then be used as input for another iteration of retraining the model. This process would be repeated until the model and the poses ceased to change significantly.

To apply the learned model to determine whether a new character is an instance of the letter 'A' (block 116), the new character would be reposed to maximize the predicted output of the neural network. If this predicted output exceeded a preset threshold, the character would be classified as an 'A,' otherwise it would be not be classified as an 'A.' If several models had been learned (e.g., one for each letter), then the new character would be reposed separately for each model, and the model that gave the highest predicted output would be applied to classify the new character.

As with molecules, the advantage of this aspect of the invention over prior methods is that rather than attempting to classify the characters in their starting poses (which are somewhat arbitrary), the invention reposes the characters so that they adopt poses most informative for recognition (i.e., poses that accentuate those aspects of the letter 'A' that are shared among all instances of 'A's and not shared by instances of other characters).

It will be understood that these two aspects of the invention do not require that a neural network learning procedure be employed. They can be applied with any procedure that constructs predictive models. It will also be understood that these two aspects of the invention are not limited to problems of assigning objects into a discrete set of classes (e.g., active vs. inactive, 'A' vs. 'B' vs. 'C' etc.). The methods can also be applied to tasks, such as drug activity prediction, in which the model must predict a real-valued property of the objects.

Further Applications

Those skilled in the art would recognize, after perusal of this application, that the invention is also applicable to a wide variety of other problems, including:

- the general problem of classifying objects into one of a plurality of categories, in response to data about those objects and in response to example objects from those categories;
- classifying written characters as one of a set of known letters or symbols, in response to image, time and pressure data about those written characters;
- classifying speech fragments as one of a set of linguistic units such as consonants, vowels, syllables or words, in response to data about pitch, tone, and volume of those speech fragments; and
- classifying pictures as one of a set of physical images, in response to image data about those physical images.

The invention has been described by reference to various embodiments. It will be understood that various modifications and changes may be made without departing from the scope of the invention which is to be limited only by the appended claims.

We claim:

1. A method for designing a molecule, said method comprising
    selecting a plurality of molecules, each one of said molecules having at least one pose;
    selecting a training set having a pose for each one of said molecules;
    constructing a model for determining a predicted result of an assay for a measure of activity relating to a set of desired physical properties for said molecule, and for determining a confidence measure for said predicted result;
    operating said model for a first pose of a first molecule in said training set to produce a predicted result and a confidence measure for said first pose;
    operating said model for a second pose of said first molecule to produce a predicted result and a confidence measure for said second pose;
    conditionally modifying said model in response to a difference between said predicted result and a result of an actual said assay conducted for said molecule;
    conditionally modifying said training set to replace said first pose with said second pose in response to a difference between said predicted result for said first pose and said predicted result for said second pose;
    repeating said steps of operating said model for said first and second poses, and conditionally modifying said model and said training set, until a predetermined condition is reached;
    operating said model for a pose of a new molecule, said new molecule not being in said training set, to produce a predicted result and a confidence measure for said new molecule;
    conditionally conducting an assay for said new molecule in response to said predicted result and said confidence measure;
    repeating said steps of operating said model for a pose of a new molecule and conditionally conducting an assay for said new molecule, until a predetermined condition is reached.

2. The method of claim 1, wherein a first predetermined condition includes no substantial change in a set of model parameter values for said model, and no substantial change in a set of poses for said model.

3. The method of claim 1, wherein said step of conditionally modifying said model employs gradient descent for a set of model parameter values.

4. The method of claim 1, wherein
    said step of conditionally modifying said model first iteratively modifies a set of model parameter values until the differences between the predicted activities of said at least some of the poses of molecules and the known activities of such molecules are minimized; and
    said step of conditionally modifying said training set then iteratively modifies the poses to maximize their activities and to obtain enhanced poses.

5. The method of claim 4, wherein each time after poses of molecules in the training set have been modified, said step of conditionally modifying said model iteratively modifies the model parameter values until the differences between the predicted activities of said at least some of the enhanced poses of molecules and the known activities of such molecules are minimized to obtain a set of modified parameter values, so that any pose modification thereafter will be in accordance with said set of modified parameter values.

6. The method of claim 1,
    wherein the pose of each molecule in the set that has higher predicted activity than other poses in the set of the same molecule defines the best pose of such molecule, and
    wherein said model parameter values are modified in said step of conditionally modifying said model in response to a comparison between predicted activities of the best poses in the set and their known activities to minimize the differences between the predicted activities of said at least some of the best poses of molecules in the set and the known activities of such molecules.

7. The method of claim 1, said model constructing step including extracting a set of feature values from each of said initial poses related to said activity and setting an initial value for each of the features to be some of the model parameter values.

8. The method of claim 7, said model constructing step further including setting initial mean and standard deviations of a feature value and a Gaussian-like function representing a contribution to predicted activity of a pose as a fuinction of said feature value in relation to its initial mean and standard deviations.

9. The method of claim 8, wherein said model constructing step further includes setting a positive or negative weighting factor for said Gaussian function.

10. The method of claim 1,
    wherein an error function is defined for each pose, said function being a difference between the predicted activity of such pose of a molecule and the known activity of such molecule,
    wherein said step of conditionally modifying said model includes deriving a total error function indicating the sum of the individual error functions of each of some of the poses and changing the model parameter values to minimize the total error function.

11. The method of claim 10, wherein said step of conditionally modifying said model employs gradient based steps to minimize the error function.

12. The method of claim 1, wherein said step of conditionally modifying said training set modifies the poses as functions of parameters including orientation and conformation parameters.

13. The method of claim 12, wherein said functions are differentiable and said step of conditionally modifying said training set includes differentiating the functions with respect to orientation and conformation parameters.

14. The method of claim 1, further comprising
setting a set of ordered numerical values according to a preset order to represent the known activities of said plurality of molecules,
wherein said step of conditionally modifying said model includes adjusting the set of ordered numerical values while retaining the preset order to reduce the differences between the predicted activities of said at least some poses of molecules in the initial or an updated training set and the known activities of such molecules.

15. The method of claim 1, further comprising, prior to the step of selecting a training set, searching for conformers of said plurality of molecules and aligning the conformers relative to one another to form possible poses.

16. The method of claim 1, wherein said step of operating said model for a pose of a new molecule indicates which conformer of said new molecule would have the highest predicted activity with respect to said chemical function.

17. The method of claim 1, wherein said step of operating said model for a pose of a new molecule indicates which properties of said new molecule would have effects on its predicted activity with respect to said chemical function.

18. The method of claim 1, further comprising visually displaying relationship between poses of molecules and model parameter values using computer graphics.

19. The method of claim 18, further comprising modifying said poses with respect to the model parameter values displayed to modify the predicted activities of the poses.

20. The method of claim 1, wherein said step of operating said model for a pose of a new molecule includes searching a database of molecules with unknown activities and predicting their activities.

21. The method of claim 1, wherein said model constructing step includes setting a sigmoid function representing a contribution to predicted activity of a pose as a sum of the weighted Gaussians of one or more individual feature values.

22. The method of claim 21, wherein said model constructing step further includes setting another sigmoid function representing the overall predicted activity of a pose as a weighted sum of the sigmoid functions.

23. A method for designing a molecule, said method comprising
operating a computer to define a plurality of molecules, each one of said molecules having at least one pose;
operating a computer to define a training set having a pose for each one of said molecules;
operating a computer to construct a model in a memory for predicting a result of an assay for a measure of activity relating to a set of desired physical properties for said molecule;
operating a computer using said model for a first pose of a first molecule in said training set to produce a prediction for said first pose;
operating a computer using said model for a second pose of said first molecule to produce a prediction for said second pose;
conditionally modifing said model in said memory in response to a difference between said prediction and a result of an actual said assay conducted for said first pose;
conditionally modifying said training set in said memory to replace said first pose with said second pose in response to a difference between said prediction for said first pose and said prediction for said second pose;
repeating said steps of operating a computer using said model for said first and second poses, and conditionally modifying said model and said training set, until a predetermined condition is reached;
operating a computer using said model for a pose of a new molecule, said new molecule not being in said training set, to produce a prediction for said pose of said new molecule;
conducting an actual said assay for said new molecule;
comparing said prediction for said pose of said new molecule with a result of said actual assay for said new molecule; and
repeating said steps of operating a computer using said model for said pose of said new molecule, conducting an actual said assay for said new molecule, and comparing said prediction, until a predetermined condition is reached.

24. A method as in claim 23, comprising conditionally modifying said model in response to a difference between said prediction for said pose of said new molecule and said result of said actual assay for said new molecule.

25. A method as in claim 23, comprising conditionally modifying said training set in response to a difference between said prediction for said pose of said new molecule and said result of said actual assay for said new molecule.

26. A method as in claim 23, comprising
operating said model for at least one pose for each one of a plurality of new molecules, said plurality of new molecules not being in said training set, to produce a prediction for each one of said plurality of new molecules,
selecting a choice one of said plurality of new molecules in response to said prediction for each one of said plurality of new molecules;
conducting an actual said assay for said choice one of said plurality of new molecules;
comparing a result of said actual assay for said choice one of said plurality of new molecules with at least a part of said prediction for each one said plurality of new molecules; and
repeating said steps of selecting a choice one, conducting an actual said assay for said choice one, and comparing a result of said actual assay for said choice one, until a predetermined condition is reached.

27. A method as in claim 26, comprising
conditionally modifying said model in response to a difference between said prediction for said choice one of said plurality of new molecules and said result of said actual assay for said choice one of said plurality of new molecules.

28. A method as in claim 26, comprising
conditionally modifying said training set in response to a difference between said prediction for said choice one of said plurality of new molecules and said result of said actual assay for said choice one of said plurality of new molecules.

29. A method as in claim 23, wherein said model comprises a neural network, said neural network comprising
a plurality of layers each having at least one node;
said plurality of layers including a first layer having at least one node coupled to an input value;

a second layer having at least one node coupled to a plurality of nodes of said first layer;

said first layer having at least one node with a first transfer function, said first transfer function comprising a Gaussian function with parameters m, s, and z, said parameters being modifiable; and said second layer having at least one node with a second transfer function, said second transfer function comprising a sigmoid function with parameters, said parameters being modifiable.

30. A method as in claim 23, wherein said new molecule is designed in response to said model.

31. A method as in claim 23, wherein said new molecule is a catalyst, a carbohydrate, a coating agent, a cosmetic, an explosive, an industrial chemical, a paint, a perfuming agent, a petroleum derivative, a polymer, or a polypeptide.

32. A method as in claim 23, wherein said new molecule is a pharmaceutical.

* * * * *